United States Patent
Min et al.

(10) Patent No.: US 11,596,796 B2
(45) Date of Patent: Mar. 7, 2023

(54) SYSTEM AND METHOD TO MANAGING STIMULATION OF SELECT A-BETA FIBER COMPONENTS

(71) Applicant: Pacesetter, Inc., Sylmar, CA (US)

(72) Inventors: Xiaoyi Min, Simi Valley, CA (US); Alexander Kent, Mountain View, CA (US); Richard Williamson, Santa Monica, CA (US)

(73) Assignee: Pacesetter, Inc., Sylmar, CA (US)

(*) Notice: Subject to any disclaimer, the term of this patent is extended or adjusted under 35 U.S.C. 154(b) by 119 days.

(21) Appl. No.: 17/008,715

(22) Filed: Sep. 1, 2020

(65) Prior Publication Data

US 2020/0391031 A1 Dec. 17, 2020

Related U.S. Application Data

(63) Continuation of application No. 15/937,427, filed on Mar. 27, 2018, now Pat. No. 10,864,372, which is a continuation of application No. 14/978,664, filed on Dec. 22, 2015, now Pat. No. 9,925,379.

(51) Int. Cl.
| | |
|---|---|
| A61N 1/36 | (2006.01) |
| A61N 1/372 | (2006.01) |
| A61N 1/05 | (2006.01) |
| A61B 5/00 | (2006.01) |
| A61B 5/24 | (2021.01) |
| A61B 5/389 | (2021.01) |

(52) U.S. Cl.
CPC ....... *A61N 1/36071* (2013.01); *A61N 1/0551* (2013.01); *A61N 1/36132* (2013.01); *A61N 1/36135* (2013.01); *A61N 1/36171* (2013.01); *A61N 1/36178* (2013.01); *A61N 1/37241* (2013.01); *A61B 5/24* (2021.01); *A61B 5/389* (2021.01); *A61B 5/7257* (2013.01)

(58) Field of Classification Search
CPC ............ A61N 1/36071; A61N 1/36135; A61N 1/36139; A61N 1/36164
See application file for complete search history.

(56) References Cited

U.S. PATENT DOCUMENTS

| | | |
|---|---|---|
| 8,340,775 B1 | 12/2012 | Cullen et al. |
| 9,409,019 B2 | 8/2016 | Walker et al. |
| 9,610,448 B2 | 4/2017 | Hou et al. |
| 9,656,077 B2 | 5/2017 | De Ridder |

(Continued)

*Primary Examiner* — George R Evanisko
(74) *Attorney, Agent, or Firm* — Norton Rose Fulbright US LLP

(57) ABSTRACT

A computer implemented method and system is provided for managing neural stimulation therapy. The method comprises under control of one or more processors configured with program instructions. The method delivers a series of candidate stimulation waveforms having varied stimulation intensities to at least one electrode located proximate to nervous tissue of interest. A parameter defines the candidate stimulation waveforms is changed to vary the stimulation intensity. The method identifies a first candidate stimulation waveform that induces a paresthesia-abatement effect, while continuing to induce a select analgesic effect. The method further identifies a second candidate stimulation waveform that does not induce the select analgesic effect. The method sets a stimulation therapy based on the first and second candidate stimulation waveforms.

30 Claims, 11 Drawing Sheets

(56) References Cited

U.S. PATENT DOCUMENTS

| | | |
|---|---|---|
| 9,925,379 B2 | 3/2018 | Min et al. |
| 10,926,092 B2 | 2/2021 | Esteller et al. |
| 2011/0184488 A1 | 7/2011 | De Ridder |
| 2015/0032181 A1* | 1/2015 | Baynham .......... A61N 1/36139 607/46 |

* cited by examiner

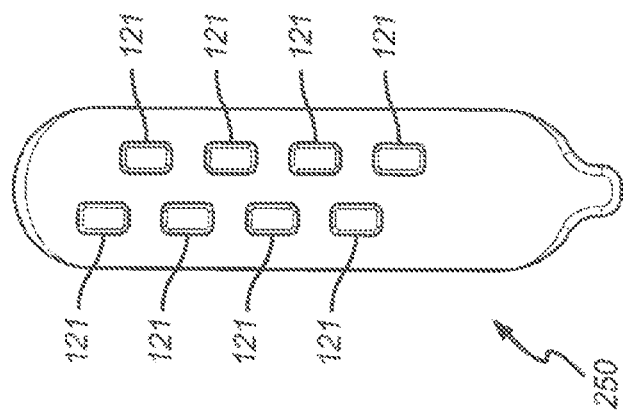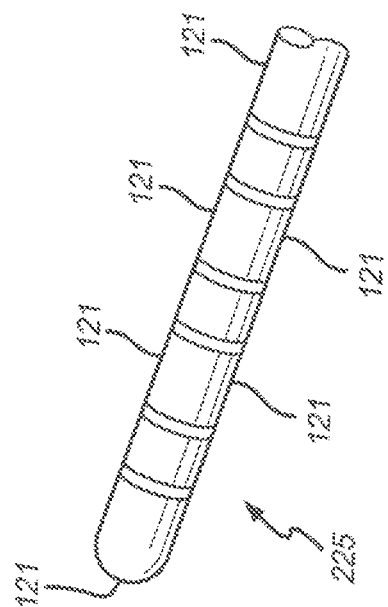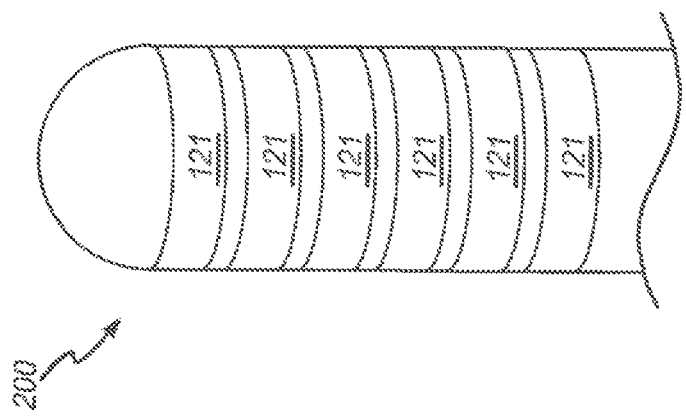

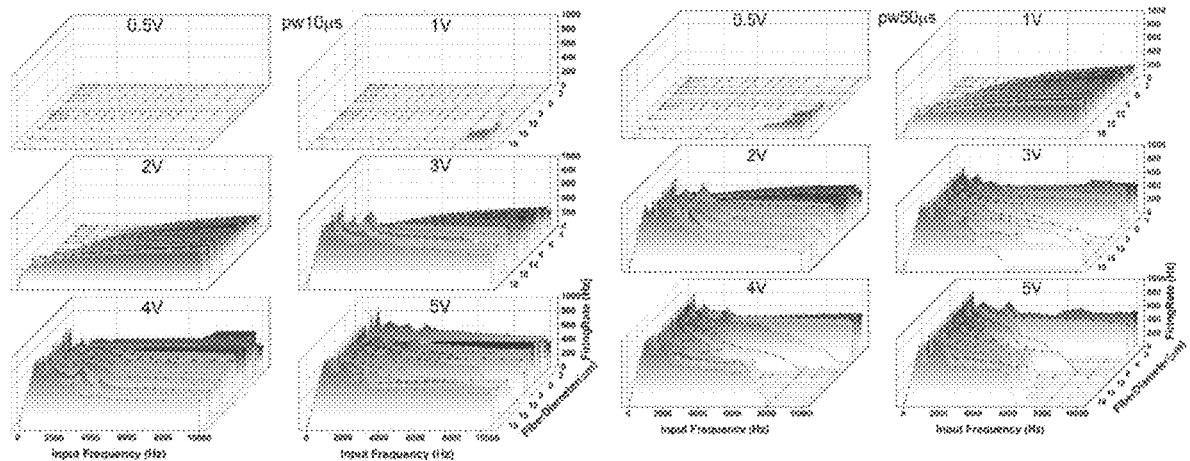
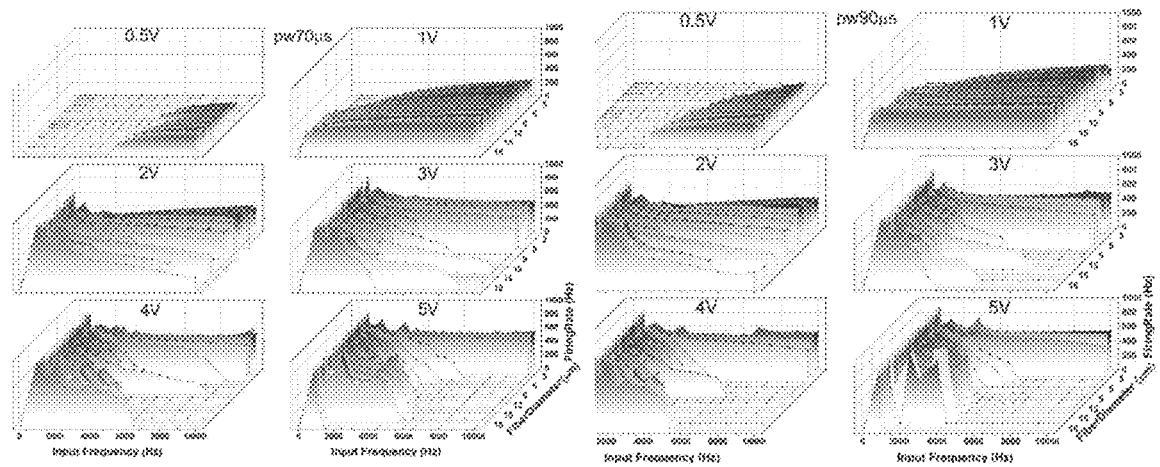
FIG. 3

SYSTEM AND METHOD TO MANAGING STIMULATION OF SELECT A-BETA FIBER COMPONENTS

RELATED APPLICATIONS

This application is a continuation of U.S. patent application Ser. No. 15/937,427, filed Mar. 27, 2018, entitled "System and Method to Managing Stimulation of Select A-Beta Fiber Components," which is a continuation of U.S. patent application Ser. No. 14/978,664, filed Dec. 22, 2015, entitled "System and Method to Managing Stimulation of Select A-Beta Fiber Components," (Now U.S. Pat. No. 9,925,379, issued Mar. 27, 2018) which are both incorporated herein by reference in their entirety.

BACKGROUND OF THE INVENTION

Spinal cord stimulation (SCS) is used to treat a wide range of chronic neuropathic pain conditions by delivering electrical stimulation to select portions of the spinal cord. In the past, SCS therapy has been proposed in which a tonic therapy is defined by single pulses have a select pulse width, frequency and intensity. By way of example, tonic therapies have been proposed to manage cervical and lumbar pain. The pulse width, frequency and intensity may be changed, along with electrode configuration and placement on the spinal column in connection with pain relief for individual patients.

NS systems are devices that generate electrical pulses and deliver the pulses to nervous tissue to treat a variety of disorders. For example, spinal cord stimulation has been used to treat chronic and intractable pain. Another example is deep brain stimulation, which has been used to treat movement disorders such as Parkinson's disease and affective disorders such as depression. While a precise understanding of the interaction between the applied electrical energy and the nervous tissue is not fully appreciated, it is known that application of electrical pulses to certain regions or areas of nervous tissue can effectively reduce the number of pain signals that reach the brain. For example, applying electrical energy to the spinal cord associated with regions of the body afflicted with chronic pain can induce "paresthesia" (a subjective sensation of numbness or tingling) in the afflicted bodily regions.

SCS therapy, delivered via epidurally implanted electrodes, is a widely used treatment for chronic intractable neuropathic pain of different origins. Traditional tonic therapy evokes paresthesia covering painful areas of a patient. During SCS therapy calibration, the paresthesia is identified and localized to the painful areas by the patient in connection with determining correct electrode placement.

Recently, new stimulation configurations such as burst stimulation and high frequency stimulation, have been developed, in which closely spaced high frequency pulses are delivered to the spinal cord in a manner that does not generate paresthesias for the majority of patients, but still affords a therapeutic result. Neuropathic pain may result from lesions or diseases affecting the peripheral or central regions of the somatosensory system, and is difficult to treat. The first spinal cord stimulator as a treatment for neuropathic pain was implanted by Shealy in 1967, which was based on the gate-control theory proposed by Melzack and Wall (1965). The gate-control theory proposed that intrinsic activation of large diameter A-beta (A.beta.) fibers blocks or inhibits the transmission of noxious stimuli to the brain via an inhibitory interneuron. It has been shown that electrical stimulation also may activate the large diameter A-beta fibers with the same result. The A-beta fibers transmit information from the peripheral nervous system through the dorsal root ganglion (DRG) before entering and projecting along the dorsal column.

Recent clinical evidence suggests that kilohertz frequency (about 0.10 kHz) spinal cord stimulation (KHFSCS) and burst spinal cord stimulation (SCS) can produce paresthesia-free analgesia (relief from pain). While evidence exists that KHFSCS or burst SCS provides an effective neuromodulation therapy for patients with chronic pain, little is known about the potential therapeutic mechanisms of action.

A need remains for methods and systems to manage neuromodulation therapy to produce paresthesia free analgesia.

SUMMARY

In accordance with one embodiment a computer implemented method is provided for managing neural stimulation therapy. The method comprises under control of one or more processors configured with program instructions. The method delivers a series of candidate stimulation waveforms having varied stimulation intensities to at least one electrode located proximate to nervous tissue of interest. A parameter defines the candidate stimulation waveforms is changed to vary the stimulation intensity. The method identifies a first candidate stimulation waveform that induces a paresthesia-abatement effect, while continuing to induce a select analgesic effect. The method further identifies a second candidate stimulation waveform that does not induce the select analgesic effect. The method sets a stimulation therapy based on the first and second candidate stimulation waveforms.

Optionally, the second candidate stimulation waveform may exhibit a stimulation intensity that blocks large and medium A-beta fibers that would otherwise induce paresthesia and analgesic effects, respectively. The stimulation therapy may block the large A-beta fibers having diameters of approximately 11.0-13.0 μm and may activate medium A-beta fibers having diameters of approximately 6.0-11.0 μm. The candidate stimulation waveform may correspond to a high frequency stimulation waveform or a burst stimulation waveform for spinal cord stimulation (SCS). The method further comprises delivering tonic SCS pulses during the stimulation therapy in combination with the high frequency stimulation waveform or burst stimulation waveform. The method may utilize current steering to direct the tonic SCS pulses to dermatomes of interest.

Optionally, the stimulation therapy includes first and second stimulation modalities. The method further comprises delivering the first and second stimulation modalities from different first and second electrode combinations. The method may comprise sensing evoked compound action potential (ECAP) signals, applying a narrow band-pass filter to the ECAP signals to filter out stimulation artifacts from KHFSCS or burst SCS candidate waveforms, performing a fast Fourier transform to the ECAP signals after the filtering operation and the identifying operations including analyzing the ECAP signals in a frequency domain.

Optionally, the analyzing includes determining a parameter setting associated with the stimulation therapy that yields ECAP signals that fit select profiles. The setting operation sets the stimulation therapy to have an intensity I based on the following equation: $I = THPF + k*(THu - RHPF)$, where k represents a constant, where THPF represents a first intensity level corresponding to a paresthesia-abatement threshold and THu represents a second intensity level corresponding to an analgesic upper threshold.

In accordance with one embodiment, a system is provided for managing neural stimulation therapy. The system comprises a lead having at least one stimulation electrode. The lead is configured to be implanted at a target position proximate to nervous tissue of interest. The system further comprises an implantable pulse generator (IPG) coupled to the lead. The IPG is configured to deliver a series of candidate stimulation waveforms having varied stimulation intensities to at least one electrode located proximate to nervous tissue of interest, wherein a parameter defining the candidate stimulation waveforms is changed to vary the stimulation intensity. The IPG identifies a first candidate stimulation waveform that induces a paresthesia-abatement effect, while continuing to induce a select analgesic effect. The IPG further identifies a second candidate stimulation waveform that does not induce the select analgesic effect. The IPG sets a stimulation therapy based on the first and second candidate stimulation waveforms.

Optionally, the first candidate stimulation waveform exhibits a stimulation intensity that blocks large diameter A-beta fibers that would otherwise induce a paresthesia effect. The second candidate stimulation waveform exhibits a stimulation intensity that blocks large and medium diameter A-beta fibers that would otherwise induce paresthesia and analgesic effects, respectively. The target stimulation therapy blocks the large A-beta fibers having diameters of approximately 11.0-13.0 μm and activates medium A-beta fibers having diameters of approximately 6.0-11.0 μm. The candidate stimulation waveform corresponds to a high frequency stimulation waveform or a burst stimulation waveform for spinal cord stimulation (SCS).

Optionally, he IPG further delivers, as the stimulation therapy, tonic SCS pulses in combination with burst SCS waveforms or kilohertz frequency SCS. The stimulation therapy represents a series of pulse bursts separated by quiescent periods, and the tonic SCS pulses are delivered during the quiescent periods.

The IPG further senses sensory evoked compound action potential (ECAP) signals from the nervous tissue of interest and may analyze the ECAP signals for ECAP activity data to identify first and second components. The first component may be indicative of ECAP activity of large diameter A-beta fibers. The second component may be indicative of ECAP activity of medium diameter A-beta fibers. The setting operation may be based on the first and second components of the activity data.

The IPG may determine a parameter setting associated with the stimulation therapy that yields ECAP activity data for which the first and second components fit within a select profile. The IPG sets the stimulation therapy to have an intensity I based on the following equation: $I=THPF+k*(THu-RHPF)$, where k represents a constant, THPF represents a first intensity level corresponding to a paresthesia-abatement threshold, and THu represents a second intensity level corresponding to an analgesic upper threshold.

BRIEF DESCRIPTION OF THE DRAWINGS

FIG. 2A depicts stimulation portions for inclusion at the distal end of lead in accordance to embodiments herein.

FIG. 2B depicts stimulation portions for inclusion at the distal end of lead in accordance to embodiments herein.

FIG. 2C depicts stimulation portions for inclusion at the distal end of lead in accordance to embodiments herein.

FIG. 3 illustrates simulation results obtained by Arie et al., showing the firing rate of A-beta fibers as a function of fiber diameter and stimulation frequency, pulse width, and amplitude (voltage) in accordance with embodiments herein.

DETAILED DESCRIPTION

Figure 1:
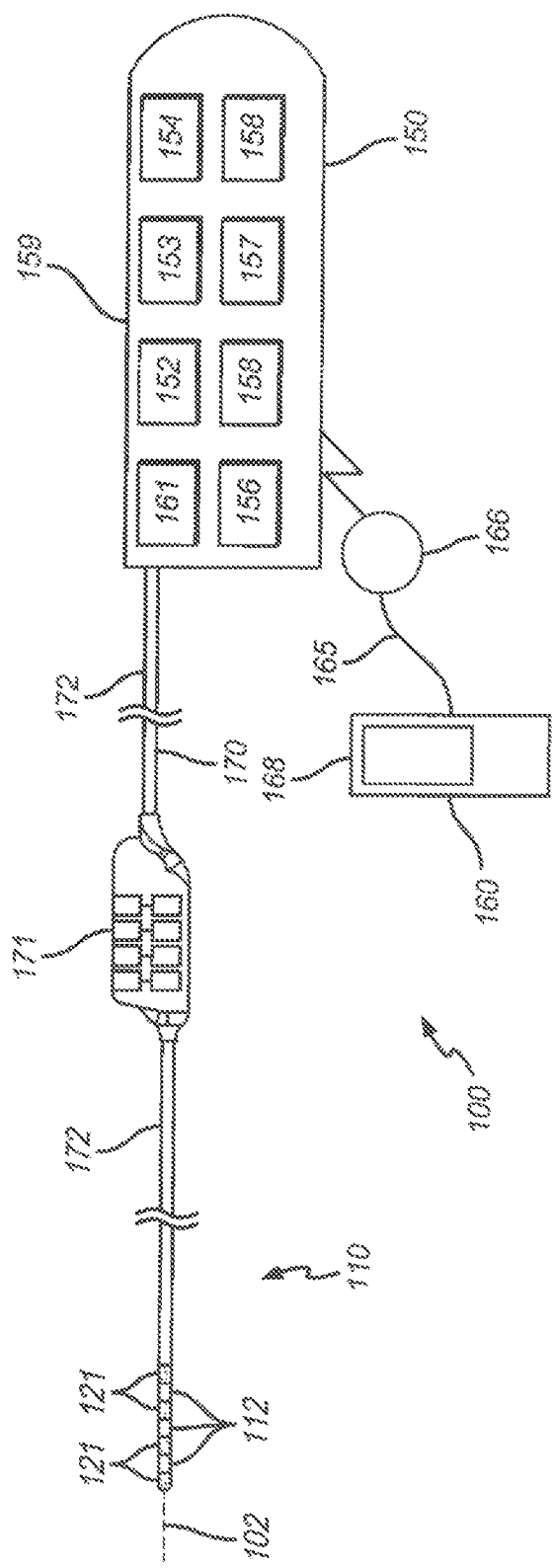
FIG. 1 depicts an NS system that generates electrical pulses for application to tissue of a patient according to one embodiment.

While multiple embodiments are described, still other embodiments of the described subject matter will become apparent to those skilled in the art from the following detailed description and drawings, which show and describe illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

The nervous system is comprised of the central nervous system (CNS) and the peripheral nervous system (PNS). The CNS contains the brain and spinal cord. The PNS is comprised mainly of mixed nerves, which are enclosed bundles of the long fibers or axons that connect the CNS to every other part of the body. Two types of nerve fibers in a mixed nerve include: sensory nerve fibers (afferent fibers sending information towards the brain) and motor nerve fibers (efferent fibers sending information from the brain). Sensory neurons transmit information from the environment, such as pain and motor neurons that mediate voluntary and involuntary movement.

In general, the peripheral nerve fibers may be classified into three types of nerve fibers based on the nerve fiber diameter and conduction velocity, namely A-, B- and C-fibers. A-fibers have large diameters, high conduction velocities, are myelinated, and are further subdivided by size and conduction velocity as A-alpha, A-beta, A-gamma and A-delta fibers. By way of example, the fast conduction velocity of the A-alpha fibers may be on the order of 80-120 m/s, and the A-alpha fibers may be on average 13-20 μm in diameter. B-fibers have diameters of about 3. mu.m and conduction velocities of 3-15 mis. C-fibers are small neurons with slow conduction velocities and are not myelinated. The A-beta fibers represent type II sensory fibers that have size generally ranging between 5.0-13.0 μm, and convey action potential (AP) signals at velocities between 30-70 mis.

It has been shown that high-frequency kilohertz spinal cord stimulation (KHFSCS) or burst SCS stimulation provides an effective neuromodulation therapy for patients with chronic pain. Recent computational modeling work by Arie et al. (Arie J E, Mei L, Carlson K W, and Shils J L. "High frequency stimulation of dorsal column axons: potential underlying mechanism of paresthesia-free neuropathic pain". Poster at International Neuromodulation Society Conference. 2015) explains that KHFSCS and burst SCS may work by blocking the large diameter A-beta fibers (11.7-13.0 μm diameter) that transmit the sensation of vibration (paresthesia), while activating medium diameter A-beta fibers (6.1-11.1 μm diameter) that generate analgesia via the gate-control theory.

FIG. 3 illustrates simulation results obtained by Arie et al., showing the firing rate of A-beta fibers as a function of fiber diameter and stimulation frequency, pulse width, and amplitude (voltage). FIG. 3 plots the neural firing rate (Hz) (along the vertical y-axis) versus fiber diameter (μm) (along the receding z-axis) versus stimulation frequency (Hz) (along the horizontal X axis). For each stimulation pulse width (pw=10 μm, 50 μm, 70 μm, or 90 μm), there are six panels showing the neural firing or action potential activity for varied stimulation amplitude (0.5 to 5 V). At low stimulation amplitudes (.about.0.5V), large fibers (>11 μm) fired only with high stimulation frequencies of 6-10 kHz (depending on the pulse width). As stimulation strength was increased (.about.1 V), neural firing of medium diameter fibers (6-11 μm) increased, and neural firing of large diameter fibers was observed at lower frequencies (<6 kHz). Most importantly, as stimulation strength was increased still further (2-5 V), the firing rate of large fibers decreased or ceased completely with high frequency stimulation (4-10 kHz), while medium fibers continued to fire (exhibit action potential activity).

In accordance with embodiments herein, methods and systems are described that select and manage stimulation parameters to entirely of substantially block large diameter A-beta fibers that otherwise transmit paresthesia (thereby achieving a paresthesia-abatement effect), while continuing to activate medium diameter A.beta. fibers to achieve a desired analgesia effect.

In accordance with embodiments herein, a programmer and/or NS system is provided that is configured to select therapy parameters that define a non-paresthesia therapy that achieves a desired analgesic effect. After implantation of the NS system, an intraoperative programming session may be conducted while the patient is awake. For example, the NS system and/or programmer may step through a series of candidate stimulation waveforms having varied stimulation intensities, determined by varying one or more parameters that define the candidate stimulation waveform. At each step in the process, the patient may be queried as to whether the patient experiences paresthesia, pain or another sensation. From the patient feedback, while testing different candidate stimulation waveforms, at least first and second candidate stimulation waveforms are identified. For example, the first candidate stimulation waveform is identified that induces a paresthesia-abatement effect (e.g. the patient experiences no or very limited paresthesia), while still experiencing a select analgesic effect (e.g. the patient experiences no pain or relatively small amount of pain at the region of interest). The second candidate stimulation waveform is identified (while receiving a different, higher stimulation intensity), at which the select analgesic effect is no longer experienced. The candidate stimulation waveforms are then used to set the stimulation therapy.

Optionally, the stimulation therapy may be set while the patient is unconscious. In accordance with embodiments herein, methods and systems measure evoked compound action potential (ECAP) signals that are conveyed by the A-beta fibers in response to each candidate stimulation waveform. The ECAP signals are recorded and analyzed (automatically or through visual inspection) by the clinician, the NS system or an external programmer device. Based on the analysis of the ECAP signals, the first and second candidate stimulation waveforms are identified, and based thereon, the stimulation therapy is set.

FIG. 1 depicts an NS system 100 that generates electrical pulses for application to tissue of a patient according to one embodiment. For example, the NS system 100 may be adapted to stimulate spinal cord tissue, peripheral nervous tissue, deep brain tissue, cortical tissue, cardiac tissue, digestive tissue, pelvic floor tissue, or any other suitable nervous tissue of interest within a patient's body. The NS system 100 may be controlled to deliver various types of non-paresthesia therapy, such as high frequency neurostimulation therapies, burst neurostimulation therapies and the like. High frequency neurostimulation includes a continuous series of monophasic or biphasic pulses that are delivered at a predetermined frequency (such as 2-1 OK). Burst neurostimulation includes short sequences of monophasic or biphasic pulses, where each sequence is separated by a quiescent period. By way of example, the pulses within each burst sequence may be delivered with an intraburst frequency of about 500 Hz. In general, non-paresthesia therapies include a continuous, repeating or intermittent pulse sequence delivered at a frequency and amplitude configured to avoid inducing (or introduce a very limited) paresthesia.

The NS system 100 may represent a closed loop neurostimulation device, where the new device is configured to provide real-time sensing functions for A-beta action potential (APs) from various locations such as a dorsal root ganglion (DRG) lead, a dorsal column lead and the like. The configuration of the lead sensing electrodes that sense action potentials from the A-beta fibers may be varied depending on the neuronal anatomy of the sensing site(s) of interest. The size and shape of electrodes is varied based on the implant location, such as the dorsal root (DR) or DRG, or the location on the implant spinal column. By way of example only, a laminectomy procedure may be used for PENTA or other paddle leads placed in SC epidural space, in order to obtain accurate action potential signals indicative of pain from the A-beta fiber. The electronic components within the NS system 100 are designed with both stimulation and sensing capabilities, including alternative non-paresthesia stimulation therapy, such as burst mode, high frequency mode and the like. The NS system 100 detects and characterizes A-beta fiber action potential signals. In one embodiment, one lead stimulates the dorsal column, the second lead senses from DRG or DR, vice versa. In another embodiment, the lead can stimulate DRG or DR or SC and sense from the same stimulation location.

The NS system 100 includes an implantable pulse generator (IPG) 150 that is adapted to generate electrical pulses for application to tissue of a patient. The IPG 150 typically comprises a metallic housing or can 159 that encloses a controller 151, pulse generating circuitry 152, a charging coil 153, a battery 154, a far-field and/or near field communication circuitry 155, battery charging circuitry 156, switching circuitry 157, memory 158 and the like. The controller 151 typically includes a microcontroller or other suitable processor for controlling the various other components of the device. Software code (program instructions) is typically stored in memory of the IPG 150 for execution by the microcontroller or processor to control the various components of the device.

The IPG 150 may comprise a separate or an attached extension component 170. If the extension component 170 is a separate component, the extension component 170 may connect with the "header" portion of the IPG 150 as is known in the art. If the extension component 170 is integrated with the IPG 150, internal electrical connections may be made through respective conductive components. Within the IPG 150, electrical pulses are generated by the pulse generating circuitry 152 and are provided to the switching circuitry 157. The switching circuitry 157 connects to outputs of the IPG 150. Electrical connectors (e.g., "Bal-Seal" connectors) within the connector portion 171 of the extension component 170 or within the IPG header may be employed to conduct various stimulation pulses. The terminals of one or more leads 110 are inserted within connector portion 171 or within the IPG header for electrical connection with respective connectors. Thereby, the pulses originating from the IPG 150 are provided to the leads 110. The pulses are then conducted through the conductors of the lead 110 and applied to tissue of a patient via stimulation electrodes 121 that are coupled to blocking capacitors. Any suitable known or later developed design may be employed for connector portion 171.

The stimulation electrodes 121 may be positioned along a horizontal axis 102 of the lead 110, and are angularly positioned about the horizontal axis 102 so the stimulation electrodes 121 do not overlap. The stimulation electrodes 121 may be in the shape of a ring such that each stimulation electrode 121 continuously covers the circumference of the exterior surface of the lead 110. Each of the stimulation electrodes 121 are separated by non-conducting rings 112, which electrically isolate each stimulation electrode 121 from an adjacent stimulation electrode 121. The non-conducting rings 112 may include one or more insulative materials and/or biocompatible materials to allow the lead 110 to be implantable within the patient. Non-limiting examples of such materials include polyimide, polyetheretherketone (PEEK), polyethylene terephthalate (PET) film (also known as polyester or Mylar), polytetrafluoroethylene (PTFE) (e.g., Teflon), or parylene coating, polyether bloc amides, polyurethane. The stimulation electrodes 121 may be configured to emit the pulses in an outward radial direction proximate to or within a stimulation target. Additionally or alternatively, the stimulation electrodes 121 may be in the shape of a split or non-continuous ring such that the pulse may be directed in an outward radial direction adjacent to the stimulation electrodes 121. The stimulation electrodes 121 SCS tonic deliver high frequency and/or burst stimulation waveforms as described herein. The electrodes 121 may also sense action potential signals for a data collection cluster. Optionally, the delivering operation may deliver the one stimulation waveform to a first sub-set of the electrodes and another stimulation waveform to a second sub-set of the electrodes, where the first and second sub-sets have at least one unique electrode relative to each other.

Optionally, the electrodes may include microelectrodes located immediately adjacent to the A-beta fibers. The method may sense A-beta fiber sensory action activity directly at the microelectrodes.

The lead 110 may comprise a lead body 172 of insulative material about a plurality of conductors within the material that extend from a proximal end of lead 110, proximate to the IPG 150, to its distal end. The conductors electrically couple a plurality of the stimulation electrodes 121 to a plurality of terminals (not shown) of the lead 110. The terminals are adapted to receive electrical pulses and the stimulation electrodes 121 are adapted to apply the pulses to the stimulation target of the patient. Also, sensing of physiological signals may occur through the stimulation electrodes 121, the conductors, and the terminals. It should be noted that although the lead 110 is depicted with four stimulation electrodes 121, the lead 110 may include any suitable number of stimulation electrodes 121 (e.g., less than four, more than four) as well as terminals, and internal conductors. Additionally or alternatively, various sensors (e.g., a position detector, a radiopaque fiducial) may be located near the distal end of the lead 110 and electrically coupled to terminals through conductors within the lead body 172.

Although not required for any embodiments, the lead body 172 of the lead 110 may be fabricated to flex and elongate upon implantation or advancing within the tissue (e.g., nervous tissue) of the patient towards the stimulation target and movements of the patient during or after implantation. By fabricating the lead body 172, according to some embodiments, the lead body 172 or a portion thereof is capable of elastic elongation under relatively low stretching forces. Also, after removal of the stretching force, the lead body 172 may be capable of resuming its original length and profile. For example, the lead body may stretch 10%, 20%, 25%, 35%, or even up or above to 50% at forces of about 0.5, 1.0, and/or 2.0 pounds of stretching force. Fabrication techniques and material characteristics for "body compliant" leads are disclosed in greater detail in U.S. Provisional Patent Application No. 60/788,518, entitled "Lead Body Manufacturing," which is expressly incorporated herein by reference.

FIGS. 2A-2C respectively depict stimulation portions 200, 225, and 250 for inclusion at the distal end of lead 110. Stimulation portion 200 depicts a conventional stimulation portion of a "percutaneous" lead with multiple ring electrodes. Stimulation portion 225 depicts a stimulation portion including several segmented electrodes. Example fabrication processes are disclosed in U.S. patent application Ser. No. 12/895,096, entitled, "METHOD OF FABRICATING STIMULATION LEAD FOR APPLYING ELECTRICAL STIMULATION TO TISSUE OF A PATIENT," which is incorporated herein by reference. Stimulation portion 250 includes multiple planar electrodes on a paddle structure. Returning to FIG. 1, for implementation of the components within the IPG 150, a processor and associated charge control circuitry for an IPG is described in U.S. Pat. No. 7,571,007, entitled "SYSTEMS AND METHODS FOR USE IN PULSE GENERATION," which is expressly incorporated herein by reference. Circuitry for recharging a rechargeable battery (e.g., battery charging circuitry 156) of an IPG using inductive coupling and external charging circuits are described in U.S. Pat. No. 7,212,110, entitled "IMPLANTABLE DEVICE AND SYSTEM FOR WIRELESS COMMUNICATION," which is expressly incorporated herein by reference.

An example and discussion of "constant current" pulse generating circuitry (e.g., pulse generating circuitry 152) is provided in U.S. Patent Publication No. 2006/0170486 entitled "PULSE GENERATOR HAVING AN EFFICIENT FRACTIONAL VOLTAGE CONVERTER AND METHOD OF USE," which is expressly incorporated herein by reference. One or multiple sets of such circuitry may be provided within the IPG 150. Different burst and/or high frequency pulses on different stimulation electrodes 121 may be generated using a single set of the pulse generating circuitry 152 using consecutively generated pulses according to a "multi-stimset program" as is known in the art. Complex pulse parameters may be employed such as those described in U.S. Pat. No. 7,228,179, entitled "Method and apparatus for providing complex tissue stimulation patterns," and International Patent Publication Number WO 2001/093953 A1, entitled "NEUROMODULATION THERAPY SYSTEM," which are expressly incorporated herein by reference. Alternatively, multiple sets of such circuitry may be employed to provide pulse patterns (e.g., tonic stimulation waveform, burst stimulation waveform) that include generated and delivered stimulation pulses through various stimulation electrodes of one or more leads 121 as is also known in the art. Various sets of parameters may define the pulse characteristics and pulse timing for the pulses applied to the various stimulation electrodes 121. Although constant current pulse generating circuitry is contemplated for some embodiments, any other suitable type of pulse generating circuitry may be employed such as constant voltage pulse generating circuitry.

The controller 151 delivers a series of candidate stimulation waveforms having varied stimulation intensities to at least one electrode located proximate to nervous tissue of interest, wherein a parameter defining the candidate stimulation waveforms is changed to vary the stimulation intensity. While stepping through different intensity levels, the controller 151 identifies a first candidate stimulation waveform that induces a paresthesia-abatement effect, while continuing to induce a select analgesic effect. While stepping through different intensity levels, the controller 151 identifies a second candidate stimulation waveform that does not induce the select analgesic effect. The controller 151 sets a stimulation therapy based on, among other things, the first and second candidate stimulation waveforms.

The controller 151 iteratively repeats the delivering and sensing operations for a group of candidate stimulation waveforms. In accordance with certain embodiments, patient feedback is utilized to identify/classify the candidate stimulation waveforms to identify one or more candidate waveform that achieves a desired paresthesia-abatement effect while maintaining a select analgesic effect. The patient feedback may also be utilized to identify/classify the candidate stimulation waveforms to identify one or more candidate waveforms that are no longer able to maintain the select analgesic effect.

Optionally, the controller 151 may perform signal analysis upon ECAP signals to automatically identify the candidate stimulation waveforms (e.g. based on profiles and frequency discrimination after converting the ECAP signals through Fast Fourier transforms to the frequency domain). The analyzing operation may utilize profiles by analyzing a feature of interest from a morphology of the ECAP signal over time, counting a number of occurrences of the feature of interest that occur within the ECAP signal over a predetermined duration, and generating the activity data based on the number of occurrences of the feature of interest.

The therapy parameters define at least one of a burst stimulation waveform or a high frequency stimulation waveform. The controller 151 may determine whether an energy content of the ECAP signal in select frequency clusters falls below a threshold or within an acceptable range (representing one type of profile), thereby indicating a paresthesia-abatement effect (e.g. that no pain or an acceptable low level of pain) is experienced by the patient.

Memory 158 stores software (program instructions) to control operation of the controller 151. The memory 158 also stores ECAP signals, therapy parameters, ECAP activity level data, sensory scores, pain scales and the like. For example, the memory 158 may save ECAP activity level data for various different candidate waveforms as applied over a short or extended period of time. A collection of ECAP activity level data is accumulated for different candidate waveforms and may be compared to identify high, low and acceptable amounts of sensory activity for the A-beta fibers that result from different candidate waveforms. The memory 158 stores a pain-activity data relation defining a relation between energy content of the ECAP signals in select frequency clusters and sensory scores indicative of pain experienced by a patient.

A controller device 160 may be implemented to charge/recharge the battery 154 of the IPG 150 (although a separate recharging device could alternatively be employed) and to program the IPG 150 on the pulse specifications while implanted within the patient. Although, in alternative embodiments separate programmer devices may be employed for charging and/or programming the NS system 100. The controller device 160 may be a processor-based system that possesses wireless communication capabilities. Software may be stored within a non-transitory memory of the controller device 160, which may be executed by the processor to control the various operations of the controller device 160. A "wand" 165 may be electrically connected to the controller device 160 through suitable electrical connectors (not shown). The electrical connectors may be electrically connected to a telemetry component 166 (e.g., inductor coil, RF transceiver) at the distal end of wand 165 through respective wires (not shown) allowing bi-directional communication with the IPG 150. Optionally, in some embodiments, the wand 165 may comprise one or more temperature sensors for use during charging operations.

The user may initiate communication with the IPG 150 by placing the wand 165 proximate to the NS system 100. Preferably, the placement of the wand 165 allows the telemetry system of the wand 165 to be aligned with the far-field and/or near field communication circuitry 155 of the IPG 150. The controller device 160 preferably provides one or more user interfaces 168 (e.g., touchscreen, keyboard, mouse, buttons, or the like) allowing the user to operate the IPG 150. The controller device 160 may be controlled by the user (e.g., doctor, clinician) through the user interface 168 allowing the user to interact with the IPG 150. The user interface 168 may permit the user to move electrical stimulation along and/or across one or more of the lead(s) 110 using different stimulation electrode 121 combinations, for example, as described in U.S. Patent Application Publication No. 2009/0326608, entitled "METHOD OF ELECTRICALLY STIMULATING TISSUE OF A PATIENT BY SHIFTING A LOCUS OF STIMULATION AND SYSTEM EMPLOYING THE SAME," which is expressly incorporated herein by reference.

Also, the controller device 160 may permit operation of the IPG 150 according to one or more therapies to treat the patient. Each therapy may include one or more sets of stimulation parameters of the pulse including pulse amplitude, pulse width, pulse frequency or inter-pulse period, pulse repetition parameter (e.g., number of times for a given pulse to be repeated for respective stimset during execution of program), biphasic pulses, monophasic pulses, etc. The IPG 150 modifies its internal parameters in response to the control signals from the controller device 160 to vary the stimulation characteristics of the stimulation pulses transmitted through the lead 110 to the tissue of the patient. NS systems, stimsets, and multi-stimset programs are discussed in PCT Publication No. WO 01/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are expressly incorporated herein by reference.

Figure 4A:
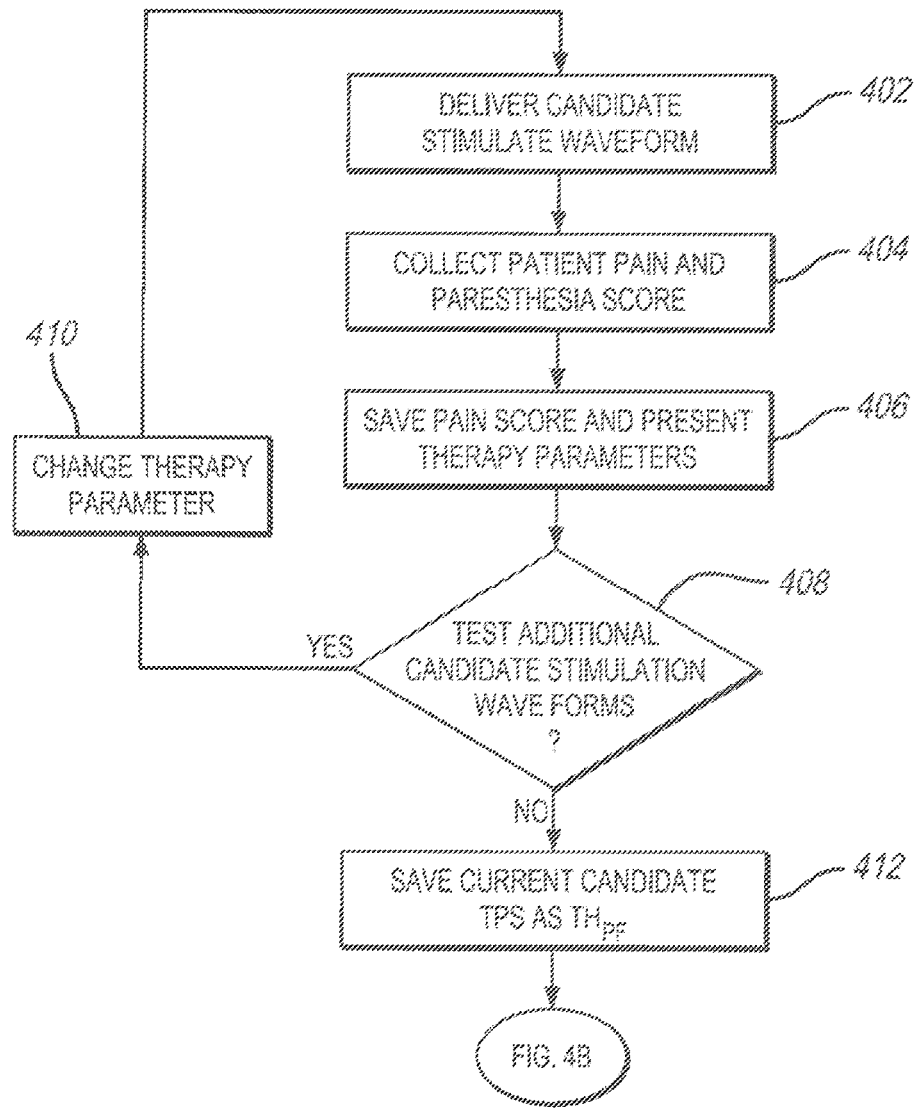
FIG. 4A illustrates a process for identifying thresholds for neural stimulation therapy in accordance with embodiments herein.
Figure 4B:
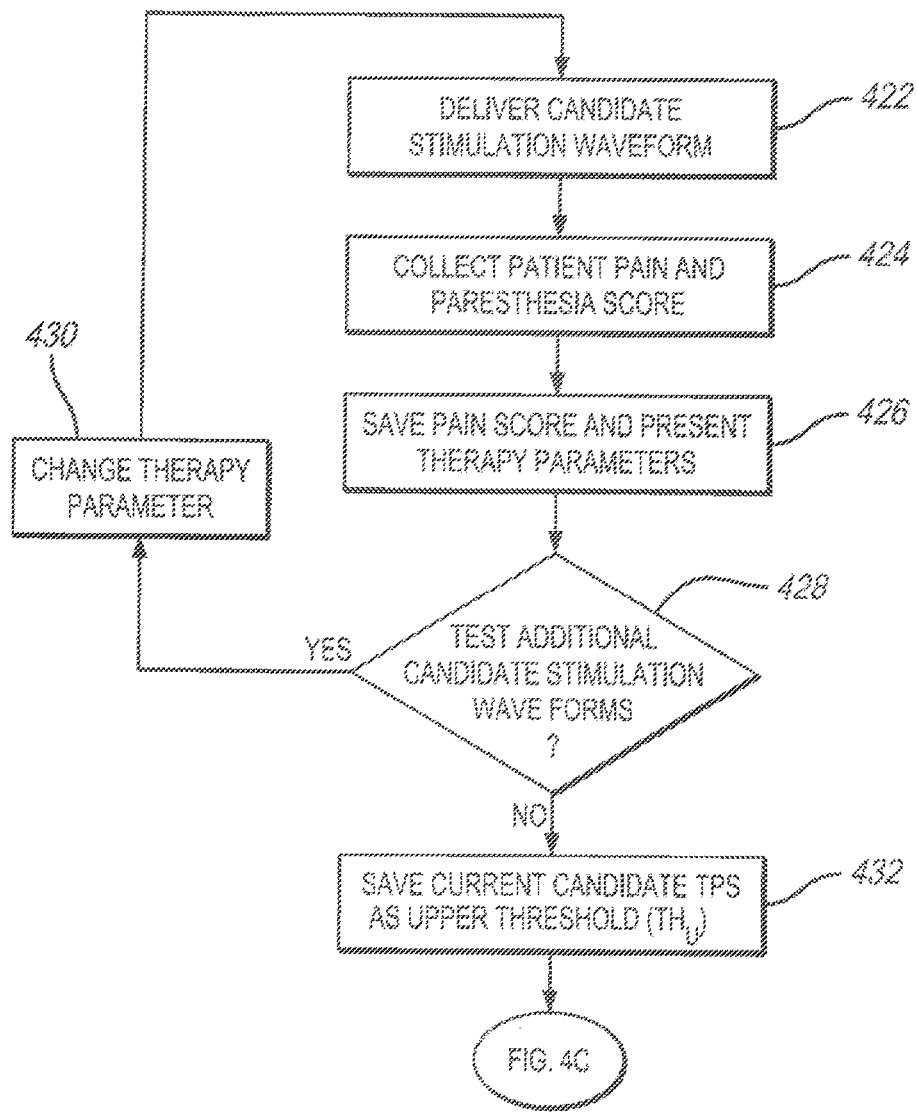
FIG. 4B illustrates a process for identifying thresholds for neural stimulation therapy in accordance with embodiments herein.
Figure 4C:
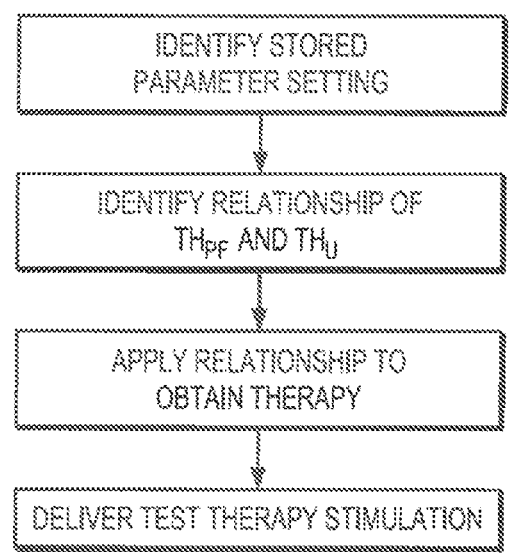
FIG. 4C illustrates the process for setting a stimulation therapy based upon thresholds identified in accordance with embodiments herein.

FIGS. 4A-4C illustrate processes for selecting and managing (e.g. burst and/or high frequency) stimulation of nervous tissue of a patient in accordance with embodiments herein. The operations of FIGS. 4A-4C may be implemented by one or more processors, such as within a controller, an implantable pulse generator, external programmer, another external device and the like. The IPG, external programmer or other external device are coupled to a lead having at least one stimulation electrode that is implanted at a target position proximate to nervous tissue of interest.

FIGS. 4A-4B illustrate a process for identifying thresholds for neural stimulation therapy in accordance with embodiments herein. At 402, the controller 151 (FIG. 1) delivers a candidate stimulation waveform to at least one electrode located proximate to nervous tissue of interest. The candidate stimulation waveform is defined by one or more parameters that determine the stimulation intensity, among other things, associated with the candidate stimulation waveform.

At 404, a patient sensory score is collected indicative of an effect induced by the candidate stimulation waveform. For example, the patient may indicate one or more ratings along one or more scales indicative of various characteristics experienced by the patient. For example, the patient may provide a rating that is indicative of an amount or degree of paresthesia experienced in a physical region of interest associated with the nervous tissue of interest. The patient may also provide a rating that is indicative of an amount or degree of pain experienced in the region of interest. Additionally or alternatively, the patient may provide a rating indicative of an amount or degree of pleasure/analgesia experienced in the region of interest.

At 406, the controller 151 saves the sensory score and the corresponding therapy parameter set. At 408, the controller determines whether additional candidate stimulation waveforms are to be tested. If so, flow branches to 410. Otherwise, flow moves to 412. The decision at 408 is based on various criteria. For example, the decision at 408 may be based on the sensory scores assigned by the patient to prior candidate stimulation waveforms. More specifically, at 408, the branching criteria may correspond to whether the patient has indicated that the present candidate stimulation waveform has induced a paresthesia-abatement effect while continuing to induce a select analgesic effect. For example, the patient may indicate, through the sensory score, that little or no paresthesia is felt, and that little or no pain is felt either. When little or no paresthesia or pain are experienced, this is interpreted as a strong indicator that the present candidate stimulation waveform is supplying a stimulation intensity that is sufficient to block larger diameter A.beta. fibers, but continues to excite medium size A beta. fibers.

At 408, when the sensory score indicates that the patient is still experiencing paresthesia, the controller 151 may determine that additional candidate stimulation waveforms should be tested. Accordingly, flow moves to 410. At 410, one or more therapy parameters are changed within a therapy parameter set. For example, the operation at 410 may change one or more of pulse amplitude, pulse width, pulse frequency or inter-pulse period, pulse repetition parameter (e.g., number of times for a given pulse to be repeated for respective stimset during execution of program), biphasic pulses, monophasic pulses, etc. The candidate stimulation waveform and therapy may represent a KHFSCS waveform/therapy or burst SCS waveform/therapy. When using KHFSCS stimulation waveforms and therapy, it may be desirable to utilize pulse widths greater than or equal to 50 μm s, as pulse widths below 50 μm s may not provide adequate block of large diameter fibers.

The operations at 402-410 are repeated for a first series of candidate stimulation waveforms in order to vary stimulation intensity by changing one or more of the therapy parameters. The operations at 402-410 are repeated until a first candidate stimulation waveform is identified that induces a paresthesia-abatement effect, while continuing to induce a select analgesic effect. When the controller 151 determines that no additional testing is warranted, namely that a candidate stimulation waveform is identified that achieves the desired combination of paresthesia abatement and analgesia, flow moves to 412. At 412, the level for one or more parameters of interest (also referred to as a therapy parameter set or TPS) is recorded as the paresthesia free threshold (THPF). Thereafter, flow advances to FIG. 4B.

The process of FIG. 4B steps through a second series of candidate stimulation waveforms to identify a second candidate stimulation waveform that induces another effect of interest. The second series of candidate stimulation waveforms corresponds to a paresthesia free "window", in which little or no paresthesia is experienced. The candidate stimulation waveforms delivered in connection with FIG. 4B are expected to block the large diameter A.beta. fibers, and thus are not expected to induce notable paresthesia. Instead, the candidate stimulation waveforms delivered in connection with FIG. 4B are used to search for a stimulation intensity that also blocks the medium diameter A.beta. fibers, thereby failing to provide an analgesia effect.

At 422, the controller 151 (FIG. 1) delivers a candidate stimulation waveform to at least one electrode located proximate to nervous tissue of interest. The candidate stimulation waveform is set to have an intensity greater than the intensity associated with the paresthesia free threshold THPF.

At 424, another patient sensory score is collected indicative of an effect induced by the candidate stimulation waveform. Again, the patient may indicate one or more ratings along one or more scales indicative of various characteristics experienced by the patient. For example, the patient may provide a rating that is indicative of an amount or degree of paresthesia, amount or degree of pain, and/or amount or degree of pleasure experienced in the region.

At 426, the controller 151 saves the sensory score and the corresponding therapy parameter set. At 428, the controller determines whether additional candidate stimulation waveforms are to be tested. If so, flow branches to 430. Otherwise, flow moves to 432. The decision at 428 is based on various criteria. For example, the decision at 428 may be based on the sensory scores assigned by the patient to prior candidate stimulation waveforms. More specifically, at 428, the criteria may correspond to whether the patient has indicated that the present candidate stimulation waveform continues to induce a select analgesic effect. For example, the patient may indicate, through the sensory score, that none, little, medium, or substantial pain is felt. When little or no pain is experienced, this is interpreted as an indicator that the present candidate stimulation waveform is supplying a stimulation intensity that is still sufficient to excite medium size A. beta. fibers. When the sensory score indicates that medium or substantial pain is felt, this is interpreted as an indication that the present candidate stimulation waveform is supplying a stimulation intensity that has begun to block the medium-size A.beta. fibers, and as such no longer provides a desired analgesic effect.

At 428, when the sensory score indicates that the patient still is not experiencing pain, the controller 151 may determine that additional candidate stimulation waveforms should be tested. Accordingly, flow moves to 430. At 430, one or more therapy parameters are changed within a therapy parameter set. Alternatively, at 428, the sensory score may indicate that the patient is experiencing an amount of pain sufficient to indicate that the candidate stimulation waveform is entirely or substantially blocking the medium-size A. beta. fibers.

The operations at 422-430 are repeated for a series of candidate stimulation waveforms in order to vary stimulation intensity by changing one or more of the therapy parameters. The operations at 422-430 are repeated until a second candidate stimulation waveform is identified that no longer induces a select analgesic effect. When the controller 151 determines that no additional testing is needed, namely that a candidate stimulation waveform is identified that has ceased to provide the select analgesic effect, flow moves to 432. At 432, the level for one or more parameters of interest is recorded as the analgesia upper threshold (THu). Thereafter, flow moves to FIG. 4C.

Optionally, the adjustment of pulse amplitude, pulse width and the like, at 410 (FIG. 4A) and 430 (FIG. 4B) may be implemented alone or in combination with adjustment of another therapy parameter, such as the number or pattern of excited electrodes, frequency and/or intra-burst frequency. For example, when utilizing KHFSCS stimulation therapies, the operations of FIGS. 4A-4B may carried out in connection with adjusting frequency each time a therapy parameter is changed at 410 and 430. By adjusting the frequency during successive attempts of candidate stimulation waveforms, the process provides a frequency scan search over a frequency range of interest (e.g., 10 kHz down to 3 kHz). The frequency scan search may be performed for determining a select (e.g., optimized) analgesia effect that limits/minimizes energy usage while maintaining paresthesia-free stimulation.

Additionally or alternatively, when utilizing burst SCS stimulation therapies, the operations of FIGS. 4A-4B may be repeated by adjusting the intra-burst frequency as one parameter changed at 410 and 430. As a further example, when adjusting frequency and/or intra-burst frequency, in combination with pulse width and/or pulse amplitude, the order in which the parameters are adjusted may be varied. For example, a series of pulse amplitudes and/or pulse widths may be tested at each frequency (for KHFSCS) or tested at each intra-burst frequency (for burst SCS). Alternatively, a series of frequencies or intra-burst frequencies may be tested at each pulse amplitude and/or pulse width. It is recognized that various combinations of parameter levels may be tested in numerous orders and combinations.

In the present example, patients enter one or more rating on a sensory score as the primary type of feedback collected in connection with each candidate stimulation waveform. Optionally, one or more additional types of feedback or tests may be performed in connection with each candidate stimulation waveform. The alternative types of feedback or tests would be tailored to identify a degree of paresthesia and analgesic effect. As explained herein, one alternative type of test that may be applied represents sensing ECAP signals and analyzing ECAP signals for characteristics of interest that are indicative of a desired paresthesia-abatement effect and analgesic effect.

In the present example, the candidate stimulation waveforms are delivered from one or more electrodes chosen to target a primary region of interest in which a patient is experiencing pain or another physiologic abnormality. Optionally, additional tests may be performed, such as utilizing alternative electrode combinations targeted to induce paresthesia-abatement and/or analgesic effects at other regions on a patient, other than the initial region of interest. For example, it may be desirable to test alternative electrode configurations to target other regions of interest when "secondary" regions of interest (e.g., leg) are found to effect pain and other sensations experienced at a primary region of interest (e.g., foot).

FIG. 4C illustrates the process for setting a stimulation therapy based upon thresholds identified in accordance with embodiments herein. For example, the stimulation therapy may be based upon the first and second candidate stimulation waveforms identified in FIGS. 4A and 4B. At 450, the controller 151 identifies the stored parameter settings that were recorded in connection with the characteristics of interest, such as in connection with the paresthesia abatement threshold THPF and analgesic upper threshold THu. At 452, the controller determines a relationship to be used when calculating the stimulation therapy based on the stored parameter settings. At 454, the controller 151 applies the relationship to obtain a stimulation therapy. By way of example, the relationship of interest may involve setting the stimulation therapy to have a stimulation intensity I based on the following equation: I=THPF+k*(THu-THPF), wherein k represents a constant (e.g., 0.2-0.8), where THPF represents a first intensity level corresponding to a paresthesia-abatement threshold and THu represents a second intensity level corresponding to an analgesic upper threshold. Optionally, alternative relationships may be used. Optionally, at 456, a test therapy stimulation may be delivered utilizing the parameters calculated at 454 to confirm that a desired effect is induced.

In accordance with embodiments herein, the operations of FIGS. 4A-4C provide an algorithm to determine the paresthesia-free stimulation parameters for KHFSCS or burst SCS. The process of FIGS. 4A-4C determine a stimulation parameter set through various operations. First, the stimulation intensity is ramped up from a low starting value (0 V or 0 mA) until the patient feels paresthesia. When the patient initially feels paresthesia, this indicates initial activation of large diameter A.beta. fibers. Next, the stimulation intensity is increased further until paresthesia disappears, which is defined as the paresthesia-abatement threshold. The paresthesia-abatement threshold represents a generally lower limit of stimulation intensity that blocks large diameter A-beta fibers and concurrent activates medium diameter A-beta fibers. It is recognized that the paresthesia-abatement threshold may correspond to more than one stimulation intensity level within a small range. For example, the threshold THPF may correspond to a point at which the patient experiences a very small amount of paresthesia. Alternatively, the threshold THPF may correspond to a point at which the patient does not experience any paresthesia, referred to as a paresthesia-free effect or point.

Once the threshold THPF is found, subsequently, the process continues to ramp up the stimulation intensity still further until pain reappears, which is defined as the analgesic upper threshold. The upper threshold is the point at which the stimulation intensity blocks both the medium and large diameter A-beta fibers from conveying non-pain inputs that would otherwise close the "gate" to the central nervous system from painful inputs. When both medium and large diameter A-beta fibers are blocked from conveying non-pain inputs, a corresponding loss of the analgesic effects of the SCS candidate stimulation waveforms occurs and the gate-control theory can no longer be used to prevent transfer of pain inputs to the central nervous system. The gate control theory of pain generally indicates that an appropriate non-painful input closes one or more "gates" to painful input. The gates represent points of entry to the central nervous system and, when closed, prevent pain sensation from reaching the brain's sensory system. Therefore, accordingly to the gate control theory of pain, stimulation by non-noxious input is able to suppress pain by preventing the pain input from entering the central nervous system. The stimulation intensities between the paresthesia-abatement threshold and the upper threshold induce non-painful inputs in a manner that takes advantage of the gate control theory. However, an upper limit exists as to the stimulation intensity that can be used to induce non-noxious inputs that close the gates to pain sensations. Stimulation intensities that exceed the upper threshold do not close the gates of the central nervous system to pain.

Accordingly, in accordance with embodiments herein, the paresthesia-abatement threshold and upper threshold are used to calculate values for one or more therapy parameters that manage a stimulation therapy to avoid introducing undesirable levels of paresthesia, while taking advantage of the gate control theory to block entry of pain to the central nervous system.

In the foregoing example, the stimulation therapy represented a KHFSCS therapy or a burst SCS therapy.

Figure 5A:
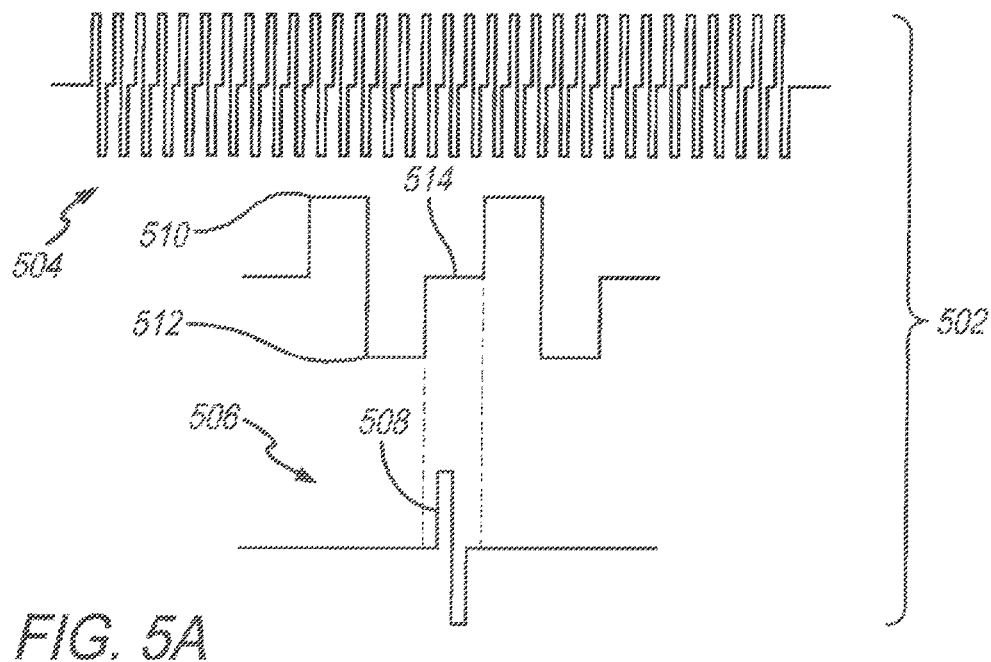
FIG. 5A illustrates hybrid therapies that may be delivered in accordance with embodiments herein.
Figure 5B:
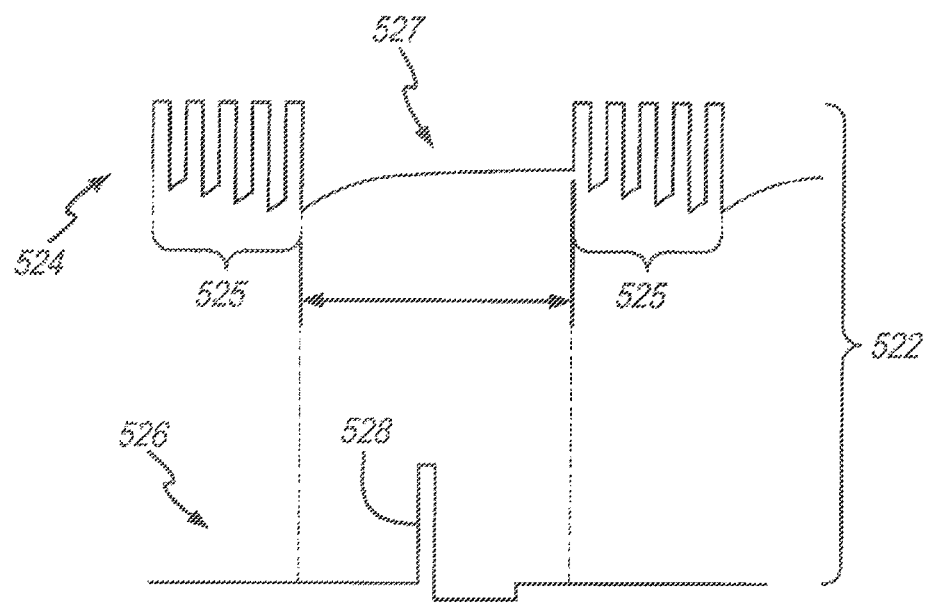
FIG. 5B illustrates hybrid therapies that may be delivered in accordance with embodiments herein.

FIGS. 5A and 5B illustrate hybrid therapies that may be delivered in accordance with embodiments herein. FIG. 5A illustrates a hybrid therapy 502 that includes a paresthesia-free KHFSCS waveform 504 combined with low-frequency tonic SCS waveform 506 (e.g., 30-100 Hz) to achieve a desired level of (e.g. optimize) analgesia coverage in the painful body dermatomes. The KHFSCS and tonic SCS waveforms 504 and 506 are combined to be delivered together simultaneously. The KHFSCS waveform 504 includes a repeating series of pulses having positive and negative phases 510 and 512, where successive pulses are separated by a quiescent period 514. The tonic SCS waveform 506 may be timed to deliver pules 508 therein during the quiescent period 514 in the KHFSCS waveform 504. Optionally, the pulse 508 in the tonic SCS waveform 506 may be delivered during one or more of the pulses in the KHFSCS waveform 504. The KHFSCS waveform 504 and tonic SCS waveform 506 may be delivered through the same electrode combinations or delivered from different combinations of electrodes.

FIG. 5B illustrates a hybrid therapy 522 that includes a burst SCS waveform 524 combined with a low-frequency tonic SCS waveform 526 (e.g. 30-100 Hz) to achieve a desired level (e.g. optimize) of analgesic coverage in the painful body dermatomes. The burst SCS and tonic SCS waveforms 524 and 526 are combined to be delivered simultaneously. The burst SCS waveform 524 includes a series of burst trains 525 separated by a quiescent period 527. The tonic SCS waveform 526 may be timed to deliver pulses 528 therein during the quiescent period 527 in the burst SCS waveform 524. Given that the inter-burst frequency between burst trains 525 is in approximately the same range as the tonic frequency, the tonic pulses 528 may be delivered between each of (or simultaneous with) the burst trains 525. The burst SCS waveform 524 and tonic SCS waveform 526 may be delivered through the same electrode combinations or delivered from different combinations of electrodes.

The hybrid therapies 502 and 522 (FIGS. 5A and 5B) each deliver two different stimulation modalities. The different stimulation modalities (KHFSCS and tonic, or burst and tonic) may be delivered from different electrode contact pairs, or from the same electrode contact pair.

In accordance with embodiments herein, the hybrid therapies 502 and 522 may be generated utilizing two stimulation sources (either current or voltage sources), where one stimulation source generates the tonic SCS waveform, while the other stimulation source generates the KHFSCS or burst SCS waveform. Optionally, a single stimulation source may be utilized, such as by providing an electronic switch, controlled by the controller 151 or a microprocessor, to apply the appropriate stimulation modality to the selected electrodes/contacts at the designated time. For example, a single current or voltage source may generate the KHFSCS or burst SCS waveform.

For hybrid stimulation, the two stimulation modalities (KHFSCS, burst SCS, and/or low-frequency tonic SCS) can be delivered using monopolar or bipolar or tripolar configurations. Optionally, the two stimulation modalities may have different stimulation amplitudes. Optionally, the hybrid therapy of KHFSCS or burst SCS, with low-frequency tonic SCS, may be delivered from a paddle SCS lead and/or percutaneous SCS lead.

Hybrid stimulation may afford relative advantages. First, the tonic SCS may be configured to steer current into the dermatomal zones within the dorsal column that correspond to patients' region of pain. For example, paresthesia mapping may be utilized with tonic SCS to obtain ideal analgesia coverage. Second, a neuronal activation threshold generally is less for low-frequency tonic SCS, as compared to KHFSCS. Accordingly, the tonic SCS may enable overall energy usage to be lower with hybrid stimulation than with KHFSCS alone. Third, simultaneous use of tonic SCS, in combination with KHFSCS or burst SCS, facilitates blocking of action potential propagation in the large fibers that generate paresthesia.

Optionally, the controller 151 may utilize current steering to direct the tonic SCS pulses to dermatomes of interest.

Figure 6:
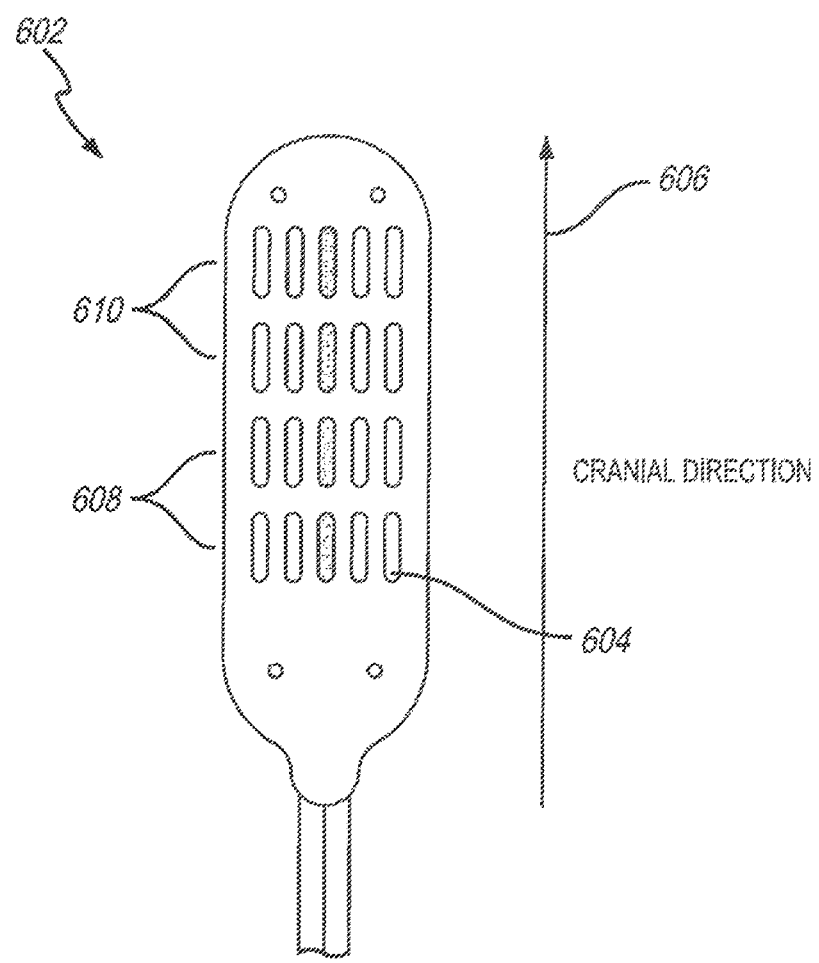
FIG. 6 illustrates an example of a portion of a lead that may be utilized in accordance with embodiments herein.

FIG. 6 illustrates an example of a portion of a lead that may be utilized in accordance with embodiments herein. The lead includes a paddle shaped distal portion 602 that retains a plurality of electrodes 604 arranged in a two-dimensional array of rows and columns. The paddle shaped distal portion 602 is oriented along the spinal column with the cranial direction extending in the direction of arrow 606. When delivering a hybrid therapy, in accordance with some embodiments, a first electrode combination 608 may be designated to deliver the tonic SCS waveform, while a second electrode combination 610 may be designated to deliver the second SCS waveform (e.g. KHFSCS or burst). In the illustrated embodiment, the second electrode combination 610 (utilized to deliver the KHFSCS or burst SCS waveform) is positioned more cranially along the distal portion 602, relative to the position of the first electrode combination 608 (utilized to deliver the tonic SCS waveform), in order to afford better blocking characteristics for action potentials propagating along the large diameter A.beta. fibers that would otherwise cause paresthesia sensations if reaching the brain.

ECAP Frequency Content Analysis

Figure 7:
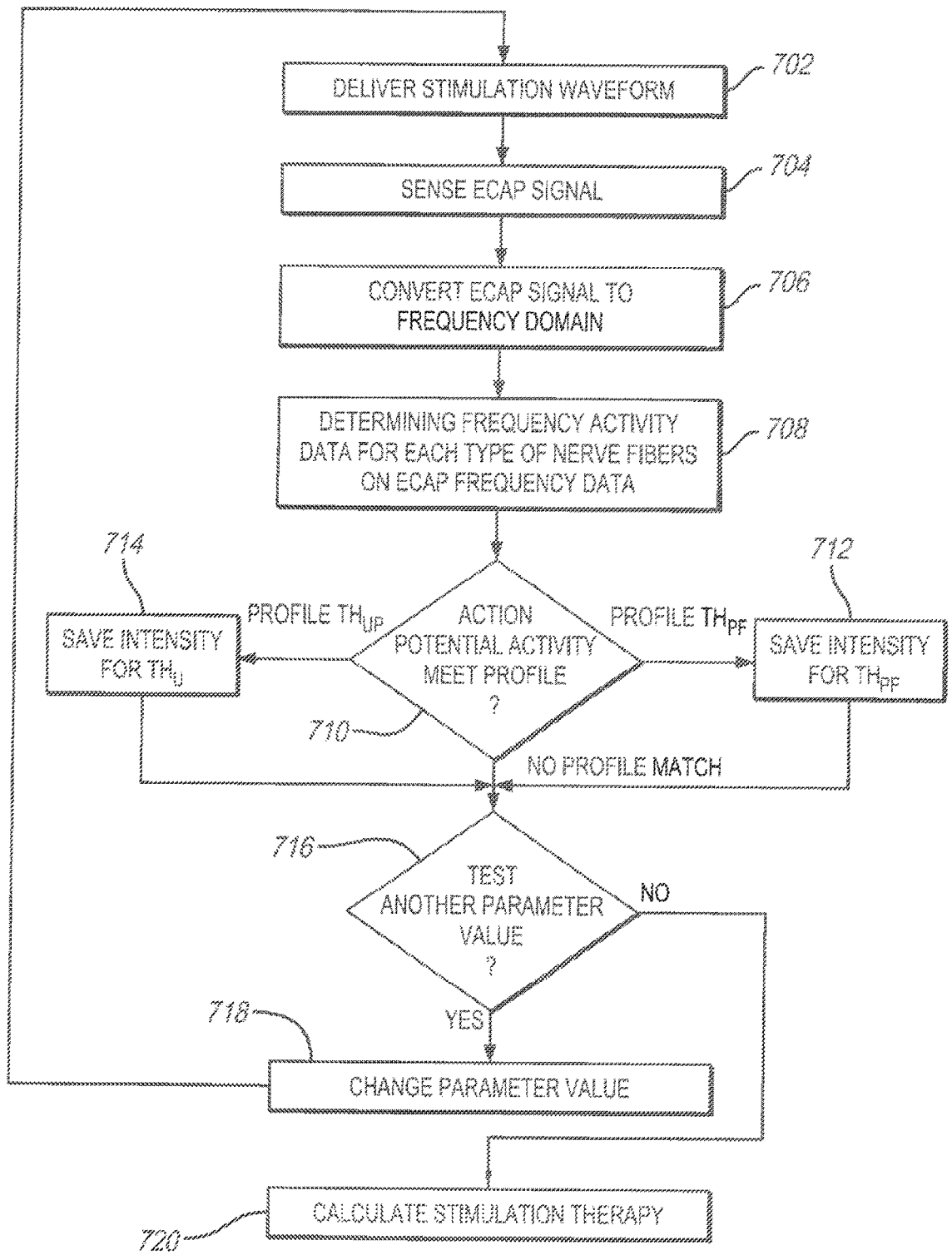
FIG. 7 illustrates a method to determine a stimulation therapy through analysis of evoked compound action potentials (ECAP) signals generated in response to candidate stimulation waveforms in accordance with embodiments herein.

FIG. 7 illustrates a method to determine a stimulation therapy through analysis of evoked compound action potentials (ECAP) signals generated in response to candidate stimulation waveforms in accordance with embodiments herein. The operations of FIG. 7 may be implemented by one or more processors, such as within an implantable pulse generator, external programmer, another external device and the like. The IPG, external programmer or other external device are coupled to a lead having at least one stimulation electrode that is implanted at a target position proximate to nervous tissue of interest. The operations of FIG. 7 may be implemented in place of, or in parallel with, the operations of FIGS. 4A and 4B.

At 702, the method defines one or more candidate stimulation waveform to be used. The candidate stimulation waveform is defined by one or more parameters forming a therapy parameter set. The method delivers a candidate stimulation waveform to at least one electrode located proximate to nervous tissue of interest. The candidate stimulation waveform is configured to excite at least medium and large diameter A.beta. fibers of the nervous tissue of interest. As explained herein, examples of parameters within a therapy parameter set (TPS) include, but are not limited to pulse amplitude, pulse width, inter-pulse delay, number of pulses per burst, pulse frequency, burst frequency, electrode configuration, electrode polarity, etc.

At 704, the controller 151 senses an ECAP signal at one or more sensing electrodes located proximate to the nervous tissue of interest. The ECAP signal represents ECAP recorded activity from afferent neurons carrying both painful stimuli, generally within the A.delta. and C fibers, and non-painful stimuli, generally within the A.beta. fibers. Optionally, a narrow band-pass filter may be applied to the ECAP signals prior to performing the FFT in order to filter out stimulation artifacts from KHFSCS or burst SCS candidate waveforms. The band-pass filter allows for extracting or isolating just the ECAP signals. For example, the ECAP signals of interest have lower frequency components (1-5 kHz) than the frequency components of the stimulation artifact (e.g., approximately 10 kHz).

At 706, the controller 151 performs frequency decomposition by analyzing a frequency content of the ECAP signal to obtain ECAP frequency data indicative of activity by medium diameter A.beta. fibers and large diameter A.beta. fibers. For example, the decomposition/analyzing operation may include using a Fast Fourier transform to convert the ECAP signal to a frequency domain to generate the ECAP frequency data. The ECAP frequency data includes clusters of frequency domain components distributed along a frequency spectrum, where each of the clusters is associated with one of the medium diameter A.beta. fibers, large diameter A.beta. fibers, A.delta. fibers and C fibers. The frequency components associated with medium diameter A.beta. fibers, large diameter A.beta. fibers, A.delta. fibers and C fibers are separate and distinct from one another. Accordingly, the frequency components associated with the A.delta. fibers and C fibers may be filtered out when not of interest.

Figure 8:
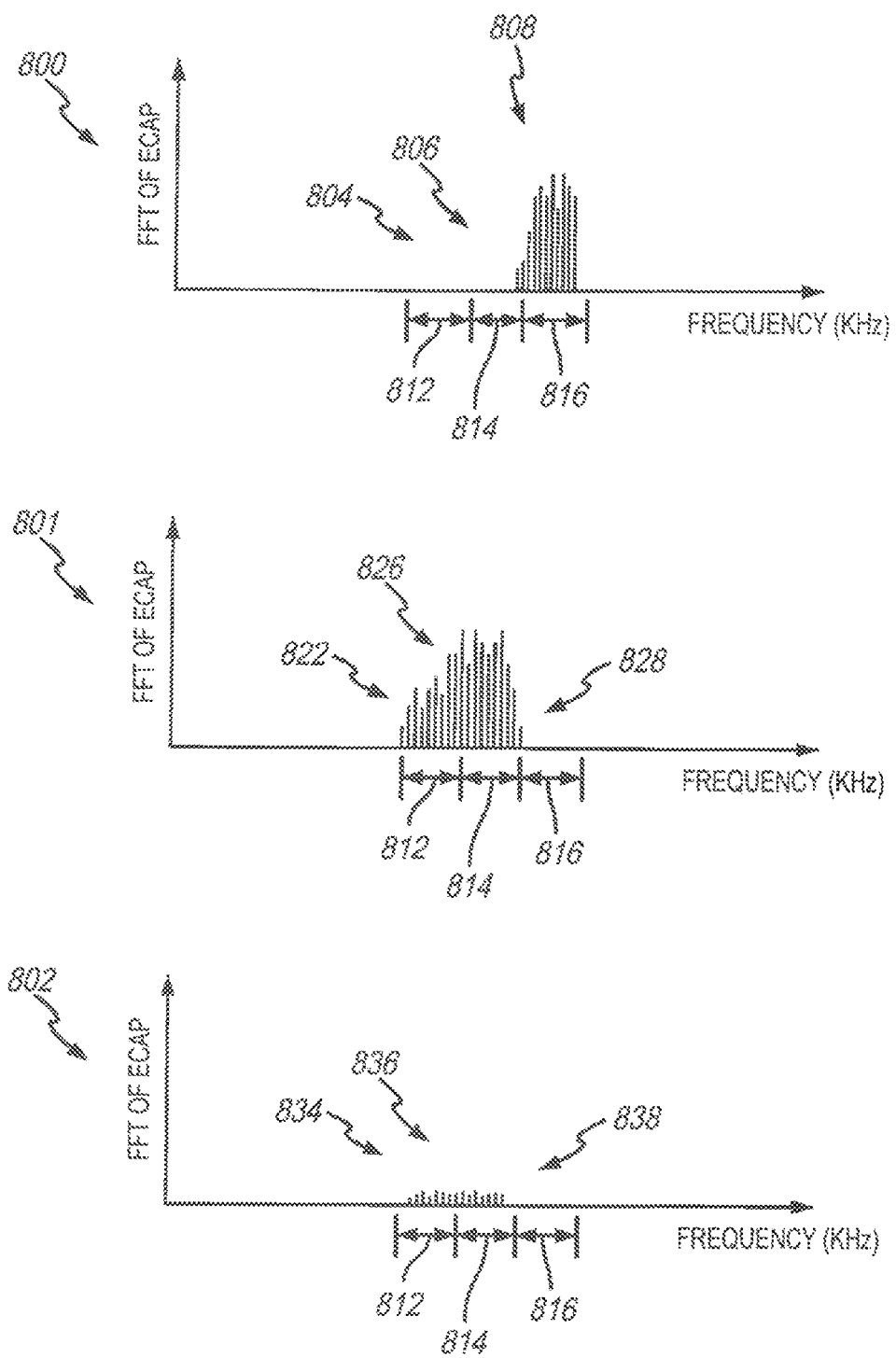
FIG. 8 illustrates examples of frequency spectrums that may be exhibited by ECAP signals when converted to the frequency domain in accordance with embodiments herein.

FIG. 8 illustrates examples of frequency spectrums 800-802 that may be exhibited by ECAP signals when converted to the frequency domain in accordance with embodiments herein. In FIG. 8, the frequency spectrums 800-802 are illustrated with the horizontal axis corresponding to individual frequencies (or frequency bin) and the vertical axis corresponding to the amount or amplitude of the action potential activity (also referred to as energy content) associated with each individual frequency (or frequency bin). The frequency spectrums 800-802 are each associated with an ECAP signal sensed over a predetermined window of time. For example, the ECAP signal may be sensed for a select window having a width of a few hundreds of microseconds. The frequency spectrums 800-802 may represent the Fast Fourier transform (FFT) of an individual window of ECAP signals, or alternatively ECAP signals collected during multiple sensing windows. The frequency spectrums 800-802 are divided into frequency ranges 812-816, each of which corresponds to a collection of frequencies or frequency bands that are associated with ECAP signals from particular size or types of fibers.

For example, with respect to the frequency spectrum 800, the high frequency range 816 is associated with ECAP signals conveyed by large diameter A. beta. fibers. The medium frequency range 814 is associated with ECAP signals conveyed by medium diameter A.beta. fibers. The low-frequency range 812 is associated with ECAP signals conveyed by medium and small diameter A.beta. fibers. The cut off frequencies between the ranges 812-816 may be manually set by an administrative person, a physician or otherwise. Optionally, the cutoff frequencies between the ranges 812-816 may be automatically determined by the NS system 100 over a period of time based on patient and physician feedback.

The frequency spectrums 800-802 include ECAP frequency data that comprises a large diameter A.beta. (LDAB) component and a medium diameter A.beta. (MOAB) component. The LDAB and MOAB components are associated with individual frequency bins grouped closely with one another in ranges 812-815 along the frequency spectrum, where the individual frequency bins have associated different amplitudes. The Fast Fourier transform converts the ECAP signals to ECAP frequency data that is separated into distinct frequency clusters 804-808, 824-828, 834-838 associated with A-beta fiber components, where each of the clusters 804-808, 824-828, 834-838 has a separate and distinct frequency range 812-816. For example, the clusters 804 and 806 (associated with the MOAB component) may be located in a low frequency range 812 and a central frequency range 814, and the cluster 808 (associated with the LDAB component) is located in a high frequency range 816 (the terms low, central and high being relative to one another). The conduction velocity of action potentials is positively related to fiber diameter, with velocities ranging between 35-75 mis across A.beta. fiber sizes. In part, because of this difference in conduction velocity, the ECAP generated by the largest A.beta. fibers may have the shortest latency and duration, whereas ECAPs generated by smaller fibers may have a longer latency and duration. When viewed from the frequency domain, the ECAP signal components resulting from large fibers would be at the higher end of the frequency distribution, lower for medium fibers, and at the low end for small fibers. Activation of different fiber sizes could therefore be distinguished in ECAPs recorded from either the DC or DRG by frequency components.

Each of the clusters 804-808, 824-828, 834-838 has an associated amount of frequency activity data. For example, each frequency bin within a cluster has a corresponding amplitude of the action potential activity associated with the frequency bin. The frequency activity data associated with an individual cluster 804-808, 824-828, 834-838 may be calculated in various manners. For example, the action potential activity data activity for any one of the clusters 804-808, 824-828, 834-838 may correspond to an average amplitude of the frequency bins therein, or alternatively, the frequency activity data may be defined by summing the activity levels for each of the frequency bins in the corresponding cluster 804-808, 824-828, 834-838 (e.g., integrating the energy within the cluster). Optionally, other mathematical factors may be used to define the activity data associated with each fiber frequency component 804-808, 824-828, and 834-838.

The frequency spectrum 800 corresponds to an ECAP signal generated in response to a candidate stimulation waveform having a low stimulation amplitude (e.g. approximately 0.5 V) and utilizing a KHFSCS waveform of approximately 6-10 kHz. The ECAP signal includes a cluster of high energy content within the high frequency cluster 808 that represent a substantial amount of excitation/firing of the large diameter A.beta. fiber component (e.g. greater than 11. mu.m). The low and medium frequency clusters 812 and 814 are substantially void or empty of energy content.

The frequency spectrum 801 corresponds to an ECAP signal generated in response to a candidate stimulation waveform having a slightly higher amplitude (as compared to the waveform utilized in connection with frequency spectrum 800). For example, the ECAP signal delivered in connection with frequency spectrum 801 may have resulted from a candidate stimulation waveform having an amplitude of 2-5 V and a high frequency of 4-10 kHz. In the example of frequency spectrum 801, the candidate stimulation waveform caused the medium diameter A.beta. fiber component to fire, while the large diameter A.beta. fiber component did not fire at all or conveyed slight energy content (also referred to as conveying no or slight action potential activity). The ECAP signal includes clusters of medium to high action potential activity within the low and medium frequency clusters 824 and 826, thereby indicating that a substantial amount of action potential activity within the ECAP signal is conveyed by the medium diameter A.beta. fiber component. The high frequency cluster 828 includes very little energy content, thereby indicating that no or relatively little action potential activity within the ECAP signal was conveyed by the large diameter A.beta. fiber component.

The frequency spectrum 802 corresponds to an ECAP signal generated in response to a candidate stimulation waveform having an amplitude of 5 V or greater and having a high frequency of 3-10 kHz. The candidate stimulation waveform resulted in very little or no action potential activity by the large diameter A.beta. fiber component and a very small amount of action potential activity by the medium diameter A.beta. fiber component. The ECAP signal includes clusters 834 and 836 having low energy content within the low and medium frequency ranges, thereby indicating that no or relatively little excitation/firing within the ECAP signal was conveyed by the medium diameter A.beta. fiber component. The frequency component 838 for the high frequency range includes no energy content, thereby indicating that no excitation/firing within the ECAP signal was conveyed by the large diameter A.beta. fiber component.

Returning to FIG. 7, at 708, the controller 151 determines the type and nature of the nerve fibers that were activated by the stimulation waveform based on the action potential activity in each of the frequency clusters or ranges. For example, the determining operation may analyze an action potential activity exhibited by the high, medium and low frequency clusters associated with each of the frequency clusters. The determination may include calculating a total activity by integrating the action potential activity at each frequency within a corresponding frequency cluster. Optionally, a maximum, average, mean or other statistical indicator of action potential activity may be identified for the action potential activity within each frequency cluster. Optionally, a morphology of the action potential activity may be determined for each of the frequency clusters.

At 710, the controller 151 compares the nature/type of action potential activity (energy content) associated with each frequency component to one or more profiles. For example, the controller 151 may compare the total activity, morphology, maximum, average, mean, etc. to one or more templates or thresholds (profiles). For example, the profiles may establish thresholds or other criteria that indicate when certain conditions exist at the A-beta fibers. The profiles may be defined as various predetermined templates or thresholds that are saved in connection with the paresthesia-abatement threshold and upper threshold. For example, one profile may correspond to the paresthesia-abatement threshold, wherein the profile is defined as a circumstance in which the high frequency component has a total activity that is below a first large diameter A-beta (LOAB) threshold, while the medium frequency component has a total activity that is above a first medium diameter a-beta (MOAB) threshold. When the total activity in the high and medium frequency components satisfy the first LOAB and MOAB thresholds, the candidate stimulation waveform is recorded as the waveform associated with the paresthesia-abatement threshold THPF.

As another example, another profile may be established for the upper threshold, such as where the profile defines a circumstance in which the high frequency component has a total activity that is below the first (or a second) LOAB threshold, while the medium frequency component has a total activity that is below a second MOAB threshold. When the total activity in the high and medium frequency components satisfy the second LOAB and MOAB thresholds, the candidate stimulation waveform is recorded as the waveform associated with the upper threshold THu. As one example, the frequency spectrum 800-802 (FIG. 8) may represent or device profiles that distinguish the thresholds THPF and THuP.

Flow branches from 710 based on whether a profile is met by the action potential activity and if so, which profile is satisfied. When the action potential activity satisfies the profile corresponding to the paresthesia-abatement threshold, flow branches to 712. When the action potential activity satisfies the profile corresponding to the analgesia upper threshold, flow branches to 714. Otherwise flow advances to 716.

At 712, the stimulation intensity associated with the candidate stimulation waveform is saved as the paresthesia-abasement threshold. At 714, the stimulation intensity associated with the candidate stimulation waveform is saved as the analgesia upper threshold. Following 712 and 714, flow advances to 716. At 716, the controller 151 determines whether additional values for one or more parameters should be tested. If so, one or more parameters are updated at 718 and flow returns to 702. If not, flow advances to 720. At 720, the stimulation therapy is set based on the paresthesia-abatement threshold and the upper threshold as discussed above in connection with FIG. 4C.

Further, due to the refractory period of neurons (1-2 ms), activation of A. beta. fibers is not expected with every stimulation pulse during delivery of a KHFSCS waveform. The refractory period of A-beta fibers mitigates issues associated with superposition of ECAP signals generated from adjacent pulses within a KHFSCS waveform.

Optionally, the process of FIG. 7 for identifying thresholds to use for setting stimulation therapy represents a frequency-domain ECAP approach. The frequency-domain ECAP approach may be used to replace patient responses and to automate the programming procedure for KHFSCS or burst SCS waveforms. The process of FIG. 7 may also be used in conjunction with hybrid therapies that combine tonic SCS pulses with paresthesia-free KHFSCS or burst SCS waveforms to optimize analgesia coverage in the painful body dermatomes.

Throughout the embodiments described herein, the same electrodes may be used for sensing and stimulation. Alternatively, one group of electrodes may be used for sensing, while a different group of electrodes are used for stimulation. For example, the sensing electrodes may be spaced apart along the lead from the stimulation electrodes. Optionally, the sensing electrodes may be provided on a separate lead unique and distinct from the lead that includes the stimulation electrodes. For example, a conventional SCS lead may be positioned along the spinal column at a desired location in order to deliver therapy at one or more stimulation sites of interest, while a separate sensing lead is provided. As one example, electrodes proximate the dorsal column may be used for stimulation, while separate electrodes proximate the dorsal root ganglion (DRG) or dorsal root (DR) are used for sensing, or vice versa. As another example, stimulation and sensing may both be performed on the dorsal column. As a further option, sensing electrodes may be located remote from the DRG or DR, such as within the torso of the body and/or along the extremities of the patient, such as within the arms and legs. Optionally, the burst stimulation waveform may be delivered at electrodes proximate both of the dorsal column and the DRG, while sensing is performed at the DRG or DR.

In various embodiments herein, conventional SCS electrodes and leads may be used for stimulation and/or sensing, provided that the SCS electrodes are configured to be located at a desired proximity relative to a target site or nervous tissue of interest. Additionally or alternatively, the lead to be used for sensing may include micro electrodes (alone or in combination with conventional SCS electrodes), where the micro electrodes are configured to be placed immediately adjacent to fibers of interest, such as A-beta fibers, A-delta fibers, and/or C-fibers.

Optionally, the ECAP signals may be analyzed in the time domain. For example, the ECAP feature of interest may represent a number of positive and negative peaks within the conduction ECAP data for a select period of time. When processing the conduction ECAP data in the time domain, the operations may include a binning operation, in which the conduction ECAP data is segmented into a series of temporal bins. Each temporal bin may include one or more occurrences of the feature of interest (e.g. spikes or peaks). The method counts a number of occurrences of the feature of interest (FOi) within each temporal bin. For example, when analyzing the conduction ECAP data in the time domain, each temporal bin may correspond to ½-1 milliseconds of ECAP data. The conduction ECAP data exhibits a number of spikes/peaks within each temporal bin, where the number of spikes/peaks is indicative of, and proportional to, an amount of sensory activity conveyed along the corresponding conduction nervous fibers. As more sensory activity is conveyed along the conduction nervous fibers, the number of spikes/peaks within the temporal bins increase. Conversely, as less sensory activity is conveyed along the conduction nervous fibers, the number of spikes/peaks within the temporal bins decreases.

Figure 9:
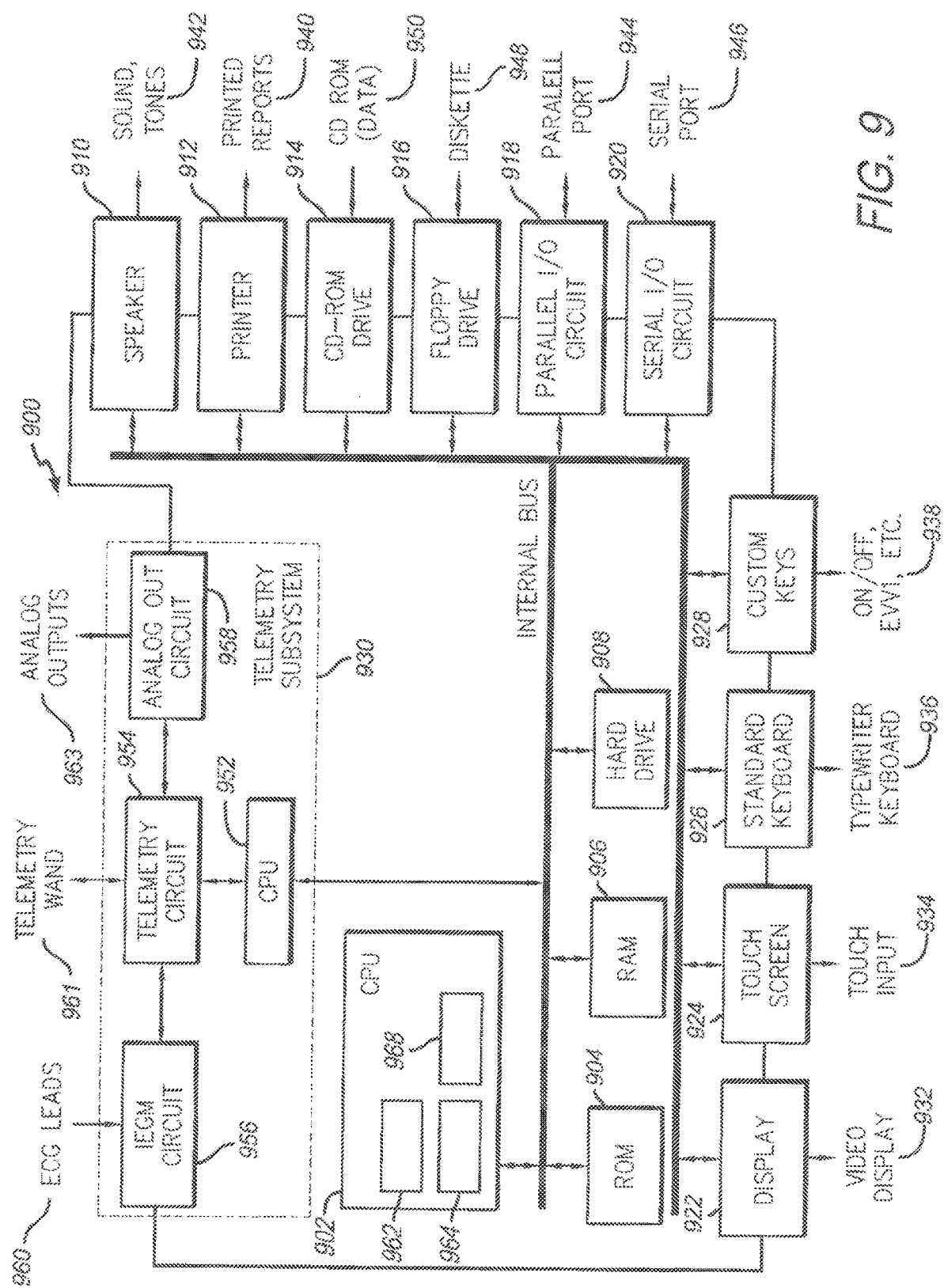
FIG. 9 illustrates a functional block diagram of an embodiment of an electronic control unit (ECU) 900 that is operated in accordance with the processes described herein.

FIG. 9 illustrates a functional block diagram of an embodiment of an electronic control unit (ECU) 900 that is operated in accordance with the processes described herein to analyze ECAP signals and to interface with one or more IPGs and/or leads with electrodes positioned at stimulation sites to deliver coupled tonic/burst therapies and/or sense sensory action potential signals. The ECU 900 may be a workstation, a portable computer, a PDA, a cell phone and the like. The ECU 900 includes an internal bus that connects/interfaces with a Central Processing Unit (CPU) 902, ROM 904, RAM 906, a hard drive 908, the speaker 910, a printer 912, a CD-ROM drive 914, a floppy drive 916, a parallel I/O circuit 918, a serial I/O circuit 920, the display 922, a touch screen 924, a standard keyboard connection 926, custom keys 928, and a telemetry subsystem 930. The internal bus is an address/data bus that transfers information between the various components described herein. The hard drive 908 may store operational programs as well as data, such as waveform templates and detection thresholds.

The CPU 902 typically includes a microprocessor, a microcontroller, or equivalent control circuitry, and may interface with an IPG and/or lead. The CPU 902 may include RAM or ROM memory, logic and timing circuitry, state machine circuitry, and I/O circuitry to interface with the IPG and/or lead. The display 922 (e.g., may be connected to the video display 932). The touch screen 924 may display graphic information relating to the CNS 110. The display 922 displays various information related to the processes described herein. The touch screen 924 accepts a user's touch input 934 when selections are made. The keyboard 926 (e.g., a typewriter keyboard 936) allows the user to enter data to the displayed fields, as well as interface with the telemetry subsystem 930. Furthermore, custom keys 928 turn on/off 938 (e.g., EWI) the ECU 900. The printer 912 prints copies of reports 940 for a physician to review or to be placed in a patient file, and speaker 910 provides an audible warning (e.g., sounds and tones 942) to the user. The parallel I/O circuit 918 interfaces with a parallel port 944. The serial I/O circuit 920 interfaces with a serial port 946. The floppy drive 916 accepts diskettes 948. Optionally, the floppy drive 916 may include a USB port or other interface capable of communicating with a USB device such as a memory stick. The CD-ROM drive 914 accepts CD ROMs 950.

The CPU 902 is configured to analyze ECAP signals collected by one or more electrodes. The CPU 902 includes a therapy circuit module 964 that is configured to control delivery of candidate and therapy waveforms. The therapy circuit module 964 is further configured to control delivery of current pulses configured as a burst SCS or KHFSCS stimulation waveform to at least one electrode and optionally tonic SCS pulses.

The CPU 902 also includes a delay adjustment circuit module 962 that adjusts the delays between and within the tonic and burst stimulation waveforms. The delay adjustment circuit module 962 also adjusts the delay between and within the KHFSCS and tonic SCS waveforms for KHFSCS plus tonic hybrid stimulation.

The CPU 902 also includes an ECAP analysis circuit module 968 that receives sensed ECAP signals from at least one electrode on the lead, and analyzes the ECAP signals as described herein.

The telemetry subsystem 930 includes a central processing unit (CPU) 952 in electrical communication with a telemetry circuit 954, which communicates with both an ECAP circuit 956 and an analog out circuit 958. The circuit 956 may be connected to leads 960. The circuit 956 may also be connected to implantable leads to receive and process ECAP signals. Optionally, the ECAP signals sensed by the leads are then transmitted, to the ECU 900, wirelessly to the telemetry subsystem 930 input.

The telemetry circuit 954 is connected to a telemetry wand 961. The analog out circuit 958 includes communication circuits to communicate with analog outputs 963. The ECU 900 may wirelessly communicate with the CNS 110 and utilize protocols, such as Bluetooth, GSM, infrared wireless LANs, HIPERLAN, 3G, satellite, as well as circuit and packet data protocols, and the like. Alternatively, a hard-wired connection may be used to connect the ECU 900 to the CNS 110.

One or more of the operations described above in connection with the methods may be performed using one or more processors. The different devices in the systems described herein may represent one or more processors, and two or more of these devices may include at least one of the same processors. In one embodiment, the operations described herein may represent actions performed when one or more processors (e.g., of the devices described herein) are hardwired to perform the methods or portions of the methods described herein, and/or when the processors (e.g., of the devices described herein) operate according to one or more software programs that are written by one or more persons of ordinary skill in the art to perform the operations described in connection with the methods.

The controller 160 may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the controllers 151 and the controller device 160 may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The controllers and the controller device may execute a set of instructions that are stored in one or more storage elements, in order to process data. The storage elements may also store data or other information as desired or needed. The storage element may be in the form of an information source or a physical memory element within the controllers and the controller device. The set of instructions may include various commands that instruct the controllers and the controller device to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. 112(f), unless and until such claim limitations expressly use the phrase "means for" followed by a statement of function void of further structure.

What is claimed is:

1. A medical device, comprising:
    at least one implantable electrode lead comprising a plurality of electrodes each configured to be electrically coupled in contact with a patient's neural tissue; and
    controller circuitry configured to:
        generate a stimulation waveform for delivery to the patient's neural tissue via one or more electrodes of the plurality of electrodes, wherein the stimulation waveform is formed to provide pain relief below a perception threshold of the patient;
        determine a neural response generated by the neural tissue in response to the stimulation waveform by averaging samples of neural activity data sensed by at least one electrode of the plurality of electrodes;
        determine at least one feature indicative of the neural response;
        compare the at least one feature to a first threshold value corresponding to a minimum stimulation to generate a pre-defined neural response and a second threshold value corresponding to the perception threshold; and
        adjust the stimulation waveform to maintain the at least one feature between the first threshold value corresponding to the minimum stimulation to generate the pre-defined neural response and the second threshold value corresponding to the perception threshold.

2. The medical device of claim 1, wherein the neural response comprises an Evoked Compound Action Potential (ECAP).

3. The medical device of claim 2, wherein the at least one feature comprises a size of the ECAP.

4. The medical device of claim 3, wherein the at least one feature comprises a height of a peak of the ECAP.

5. The medical device of claim 3, wherein the at least one feature comprises an area of the ECAP or the at least one feature comprises an ECAP peak.

6. The medical device of claim 2, wherein the at least one feature comprises a time defining a duration of a portion of the ECAP.

7. The medical device of claim 1, wherein the controller circuitry is configured to determine the at least one feature of the neural response by performing a comparison using the at least one feature and at least one threshold.

8. The medical device of claim 7, wherein the controller circuitry is configured to receive user input, and wherein the controller circuitry is configured to adjust the at least one threshold based on the user input.

9. The medical device of claim 8, wherein the controller circuitry is configured to receive the user input from an external controller.

10. The medical device of claim 1, wherein the controller circuitry is further configured to use filtering to extract the neural response.

11. A medical device, comprising:
at least one implantable electrode lead comprising a plurality of electrodes each configured to be electrically coupled in contact with a patient's neural tissue; and
controller circuitry configured to:
generate a stimulation waveform for delivery to the patient's neural tissue via one or more electrodes of the plurality of electrodes, wherein the stimulation waveform is formed to provide pain relief below a perception threshold of the patient;
determine a neural response generated by the neural tissue in response to the stimulation waveform by averaging signals sensed by at least one electrode of the plurality of electrodes;
determine at least one feature indicative of the neural response;
compare the at least one feature to a first threshold value corresponding to a minimum stimulation to generate a pre-defined neural response and a second threshold value corresponding to the perception threshold; and
adjust the stimulation waveform to maintain the at least one feature between the first threshold value corresponding to the minimum stimulation generating the pre-defined neural response detected by the signal averaging and the second threshold value corresponding to the perception threshold.

12. The medical device of claim 11, wherein the neural response comprises an Evoked Compound Action Potential (ECAP).

13. The medical device of claim 12, wherein the at least one feature comprises a size of the ECAP.

14. The medical device of claim 13, wherein the at least one feature comprises a height of a peak of the ECAP.

15. The medical device of claim 13, wherein the at least one feature comprises an area of the ECAP or the at least one feature comprises an ECAP peak.

16. The medical device of claim 12, wherein the at least one feature comprises a time defining a duration of a portion of the ECAP.

17. The medical device of claim 11, wherein the controller circuitry is configured to determine the at least one feature of the neural response by performing a comparison using the at least one feature and at least one threshold.

18. The medical device of claim 17, wherein the controller circuitry is configured to receive user input, and wherein the controller circuitry is configured to adjust the at least one threshold based on the user input.

19. The medical device of claim 18, wherein the controller circuitry is configured to receive the user input from an external controller.

20. The medical device of claim 11, wherein the controller circuitry is further configured to use filtering to extract the neural response.

21. A medical device, comprising:
at least one implantable electrode lead comprising a plurality of electrodes each configured to be electrically coupled in contact with a patient's neural tissue; and
controller circuitry configured to:
generate a stimulation waveform for delivery to the patient's neural tissue via one or more electrodes of the plurality of electrodes, wherein the stimulation waveform is formed to provide pain relief below a perception threshold of the patient;
determine a neural response generated by the neural tissue in response to the stimulation waveform sensed by at least one electrode of the plurality of electrodes;
determine at least one feature indicative of the neural response;
compare the at least one feature to a first threshold value and a second threshold value, wherein the first threshold value corresponds to a minimum stimulation by the stimulation waveform that generates a pre-defined neural response determined by averaging signals sensed by the at least one electrode of the plurality of electrodes, and wherein the second threshold value corresponds to the perception threshold; and
adjust the stimulation waveform to maintain the at least one feature between the first threshold value and the second threshold value.

22. The medical device of claim 21, wherein the neural response comprises an Evoked Compound Action Potential (ECAP).

23. The medical device of claim 22, wherein the at least one feature comprises a size of the ECAP.

24. The medical device of claim 23, wherein the at least one feature comprises a height of a peak of the ECAP.

25. The medical device of claim 23, wherein the at least one feature comprises at least one of an area of the ECAP or the at least one feature comprises an ECAP peak.

26. The medical device of claim 22, wherein the at least one feature comprises a time defining a duration of a portion of the ECAP.

27. The medical device of claim 21, wherein the controller circuitry is configured to determine the at least one feature of the neural response by performing a comparison using the at least one feature and at least one threshold.

28. The medical device of claim 27, wherein the controller circuitry is configured to receive user input, and wherein the controller circuitry is configured to adjust the at least one threshold based on the user input.

29. The medical device of claim 28, wherein the controller circuitry is configured to receive the user input from an external controller.

30. The medical device of claim 21, wherein the controller circuitry is further configured to use filtering to extract the neural response.

* * * * *

UNITED STATES PATENT AND TRADEMARK OFFICE
CERTIFICATE OF CORRECTION

PATENT NO. : 11,596,796 B2
APPLICATION NO. : 17/008715
DATED : March 7, 2023
INVENTOR(S) : Xiaoyi Min et al.

Page 1 of 1

It is certified that error appears in the above-identified patent and that said Letters Patent is hereby corrected as shown below:

In the Claims

At Column 26, Claim number 25, Line number 47, delete "comprises at least one of an area" and replace with --comprises an area--.

Signed and Sealed this
Eighteenth Day of April, 2023

Katherine Kelly Vidal
*Director of the United States Patent and Trademark Office*